United States Patent
Nauman et al.

(10) Patent No.: US 9,155,607 B2
(45) Date of Patent: Oct. 13, 2015

(54) COMPOSITIONS AND METHODS FOR REPAIR OR REGENERATION OF SOFT TISSUE

(71) Applicant: PURDUE RESEARCH FOUNDATION, West Lafayette, IN (US)

(72) Inventors: Eric Allen Nauman, West Lafayette, IN (US); Darryl Dickerson, West Lafayette, IN (US); Jocelyn Teresia Dunn, Lafayette, IN (US)

(73) Assignee: Purdue Research Foundation, West Lafayette, IN (US)

( * ) Notice: Subject to any disclaimer, the term of this patent is extended or adjusted under 35 U.S.C. 154(b) by 70 days.

(21) Appl. No.: 13/679,248

(22) Filed: Nov. 16, 2012

(65) Prior Publication Data

US 2013/0123939 A1  May 16, 2013

Related U.S. Application Data

(60) Provisional application No. 61/560,684, filed on Nov. 16, 2011.

(51) Int. Cl.
| | | |
|---|---|---|
| *A61F 2/02* | (2006.01) | |
| *A61L 27/36* | (2006.01) | |
| *A61F 2/28* | (2006.01) | |
| *A61L 27/34* | (2006.01) | |
| *A61L 27/38* | (2006.01) | |
| *A61L 27/48* | (2006.01) | |
| *A61L 27/54* | (2006.01) | |

(52) U.S. Cl.
CPC ... *A61F 2/02* (2013.01); *A61F 2/28* (2013.01); *A61L 27/34* (2013.01); *A61L 27/3608* (2013.01); *A61L 27/3687* (2013.01); *A61L 27/3804* (2013.01); *A61L 27/3834* (2013.01); *A61L 27/48* (2013.01); *A61L 27/54* (2013.01); *A61L 2430/34* (2013.01)

(58) Field of Classification Search
None
See application file for complete search history.

(56) References Cited

U.S. PATENT DOCUMENTS

| | | | |
|---|---|---|---|
| 5,112,354 A | 5/1992 | Sires | |
| 6,290,718 B1 | 9/2001 | Grooms et al. | |
| 6,332,779 B1 | 12/2001 | Boyce et al. | |
| 6,616,698 B2 | 9/2003 | Scarborough | |
| 8,029,575 B2 | 10/2011 | Borden | |
| 2004/0243242 A1* | 12/2004 | Sybert et al. | 623/17.16 |
| 2007/0087059 A1 | 4/2007 | Everaerts et al. | |
| 2008/0058953 A1 | 3/2008 | Scarborough | |
| 2008/0076176 A1 | 3/2008 | Dominko et al. | |
| 2010/0266559 A1* | 10/2010 | Nataraj et al. | 424/93.7 |
| 2011/0066241 A1 | 3/2011 | Nauman et al. | |
| 2011/0118850 A1 | 5/2011 | Govil et al. | |
| 2014/0170232 A1* | 6/2014 | Shelby et al. | 424/549 |

FOREIGN PATENT DOCUMENTS

WO  WO 2009036279 A1 * 3/2009

OTHER PUBLICATIONS

Fiegel et al. "Fetal and adult liver stem cells for liver regeneration and tissue engineering", Journal of Cellular and Molecular Medicine 10(3): 577-587, 2006.*
Sonavane et al. "In vitro permeation of gold nanoparticles through rat skin and rat intestine: effect of particle size", Colloids and Surfaces B: Biointerfaces 65: 1-10, 2008.*
Capila et al., 'Heparin—protein interactions.' Angew. Chem. Int. Ed., vol. 41, pp. 390-412, 2002.
Caplan, 'Mesenchymal stem cells,' Journal of Orthopaedic Research, vol. 9, No. 5, pp. 641-650, 1991.
Dayoub et al., 'Human mesenchymal stem cells transduced with recombinant bone morphogenetic protein-9 adenovirus promote osteogenesis in rodents,' Tissue Engineering, vol. 9, No. 2, pp. 347-356, 2003.
Evans et al., 'Clinical long-term in vivo evaluation of poly(L-lactic acid) porous conduits for peripheral nerve regeneration,' J. Biomater. Sci. Polymer Edn., vol. 11, No. 8, pp. 869-878, 2000.
Fu et al., 'Visual evidence of acidic environment within degrading poly(lactic-co-glycolic acid) (PLGA) microspheres,' Pharmaceutical Research, vol. 17, No. 1, pp. 100-106, 2000.
Gentleman et al., 'Operating curves to characterize the contraction of fibroblast-seeded collagen gel/collagen fiber composite biomaterials: effect of fiber mass,' Collagen Composites, vol. 119, No. 2, pp. 508-516, 2004.
Gentleman et al., 'Short collagen fibers provide control of contraction and permeability in fibroblast-seeded collagen gels,' Tissue Engineering, vol. 10, No. 3/4, pp. 421-427, 2004.
Golub et al., 'Sustained VEGF delivery via PLGA nanoparticles promotes vascular growth,' Am J Physiol Heart Circ Physiol, vol. 298, pp. H1959-H1965, 2010.
Gossler et al., 'Transgenesis by means of blastocyst-derived embryonic stem cell lines,' Proc. Natl. Acad. Sci. USA, vol. 83, pp. 9065-9069, Dec. 1986.
Grompe, 'The role of bone marrow stem cells in liver regeneration,' Semin Liver Dis, vol. 23, No. 4, pp. 363-372, 2003.
He et al., 'Fabrication and endothelialization of collagen-blended biodegradable polymer nanofibers: potential vascular graft for blood vessel tissue engineering,' Tissue Engineering, vol. 11, No. 9/10, pp. 1574-1588, 2005.

(Continued)

*Primary Examiner* — Ruth Davis
*Assistant Examiner* — Emily Cordas
(74) *Attorney, Agent, or Firm* — Valauskas Corder LLC

(57) ABSTRACT

Disclosed are bioscaffolds and methods for use in soft tissue repair.

19 Claims, 6 Drawing Sheets

(56) References Cited

OTHER PUBLICATIONS

Holy et al., 'In vitro degradation of a novel poly(lactide-co-glycolide) 75/25 foam,' Biomaterials, vol. 20, pp. 1177-1185, 1999.

Hui et al., 'Fluid conductance of cancellous bone graft as a predictor for graft-host interface healing,' J. Biomechanics, vol. 29, No. 1, pp. 123-132, 1996.

Inamori et al., 'An approach for formation of vascularized liver tissue by endothelial cell-covered hepatocyte spheroid integration,' Tissue Engineering, vol. 15, No. 8, pp. 2029-2037, 2009.

Jain et al., 'Engineering vascularized tissue,' Nature Biotechnology, vol. 23, No. 7, pp. 821-823, Jul. 2005.

Keuren et al., 'Covalently-bound heparin makes collagen thromboresistant,' Arterioscler. Thromb. Vasc. Biol., pp. 613-167, Mar. 2004.

Kim et al., 'Burden of liver disease in the United States: summary of workshop,' Hepatology, pp. 227-242, Jul. 2002.

Lewus et al., 'In vitro characterization of a bone marrow stem cell-seeded collagen gel composite for soft tissue grafts: effects of fiber number and serum concentration,' Tissue Engineering, vol. 11, No. 7/8, pp. 1015-1022, 2005.

Lo et al., 'Lessons learned from one hundred right lobe living donor liver transplants,' Annals of Surgery, vol. 240, No. 1, pp. 151-158, Jul. 2004.

Marcos et al., 'Single-center analysis of the first 20 adult-to-adult living donor liver transplants using the right lobe,' Liver Transplantation, vol. 6, No. 3, pp. 296-301, May 2000.

Marcos, 'Right lobe living donor liver transplantation: a review,' Liver Transplantation, vol. 6, No. 1, pp. 3-20, Jan. 2000.

Matsumoto et al., 'Liver organogenesis promoted by endothelial cells prior to vascular function,' Science, vol. 294, pp. 559-563, Oct. 19, 2001.

Meng et al., 'The effect of a layer-by-layer chitosan-heparin coating on the endothelialization and coagulation properties of a coronary stent system,' Biomaterials, vol. 30, pp. 22276-2283, 2009.

Miller et al., 'One hundred nine living donor liver transplants in adults and children: a single-center experience,' Annals of Surgery, vol. 234, No. 3, pp. 301-312, 2001.

Montesano et al., 'Transforming growth factor beta stimulates collagen-matrix contraction by fibroblasts: implications for wound healing,' Proc. Natl. Acad. Sci. USA, vol. 85, pp. 4894-4897, Jul. 1988.

Moon et al., 'Vascularization of engineered tissues: approaches to promote angiogenesis in biomaterials,' Current Topics in Medicinal Chemistry, vol. 8, No. 4, pp. 300-310, 2008.

Nauman et at., 'Dependence of intertrabecular permeability on flow direction and anatomic site,' Annals of Biomedical Engineering, vol. 27, pp. 517-524, 1999.

O'Brien et al., 'The effect of pore size on cell adhesion in collagen-GAG scaffolds,' Biomaterials, vol. 26, pp. 433-41, 2005.

Palmes et al., 'Animal models of liver regeneration,' Biomaterials, vol. 25, pp. 1601-1611, 2004.

Pieper et al., 'Preparation and characterization of porous crosslinked collagenous matrices containing bioavailable chondroitin sulphate,' Biomaterials, vol. 20, pp. 847-858, 1999.

Reing et al., 'Degradation products of extracellular matrix affect cell migration and proliferation,' Tissue Engineering, vol. 15, No. 3, pp. 605-614, 2009.

Sander et al., 'Examination of continuum and micro-structural properties of human vertebral cancellous bone using combined cellular solid models,' Biomech Model Menchanobiol, vol. 2, pp. 97-107, 2003.

Sander et al., 'Solvent effects on the microstructure and properties of 75/25 poly(D,L-lactide-co-glycolide) tissue scaffolds,' Wiley InterScience, http://tulane.edu/sse/polyRMC/publications/upload/30109_ftp.pdf, 2004.

Sellaro et al., 'Maintenance of hepatic sinusoidal endothelial cell phenotype in vitro using organ-specific extracellular matrix scaffolds,' Tissue Engineering, vol. 13, No. 9, pp. 2301-2310, 2007.

Sellaro et al., 'Maintenance of human hepatocyte function in vitro by liver-derived extracellular matrix gels,' Tissue Engineering Part A 16(3): 1075-1082, 2010.

Shimko et al., 'Comparison of in vitro mineralization by murine embryonic and adult stem cells cultured in an osteogenic medium,' Tissue Engineering, vol. 10, No. 9/10, pp. 1386-1398, 2004.

Steffens et al., 'Modulation of angiogenic potential of collagen matrices by covalent incorporation of heparin and loading with vascular endothelial growth factor,' Tissue Engineering, vol. 10, No. 9/10, pp. 1502-1509, 2004.

Teng et al., 'Functional recovery following traumatic spinal cord injury mediated by a unique polymer scaffold seeded with neural stem cells,' Proc Natl Aced Sci USA, vol. 99, No. 5, pp. 3024-3029, Mar. 5, 2002.

Thomson et al., 'Biodegradable polymer scaffolds to regenerate organs,' Advances in Polymer Science, vol. 122, pp. 247-274, 1995.

Thomson et al., 'Guided tissue fabrication from periosteum using preformed biodegradable polymer scaffolds,' Biomaterials, vol. 20, pp. 2007-2018, 1999.

Vaz et al., 'Design of scaffolds for blood vessel tissue engineering using a multi-layering electrospinning technique,' Acta Biomaterialia 1, pp. 575-582, 2005.

Wagers et al., 'Plasticity of adult stem cells,' Cell, vol. 116, pp. 639-648, Mar. 5, 2004.

Yamamoto et al., 'A comparative analysis of the transcriptome and signal pathways in hepatic differentiation of human adipose mesenchymal stem cells,' FEBS Journal, vol. 275, pp. 1260-1273, 2008.

Yang et al., 'The design of scaffolds for use in tissue engineering. Part II. Rapid prototyping techniques,' Tissue Engineering, vol. 8, No. 1, pp. 1-11, 2002.

Yannas et al., 'Synthesis and characterization of a model extracellular matrix that induces partial regeneration of adult mammalian skin,' Proc Natl Acad Sci USA, vol. 86, pp. 944-937, Feb. 1989.

Yao et al., 'The impact of proteinase-induced matrix degradation on the release of VEGF from heparinized collagen matrices,' Biomaterials, vol. 27, pp. 1608-1616, 2006.

Yoo et al., 'The chondrogenic potential of human bone-marrow-derived mesenchymal progenitor cells,' J Bone Joint Surg Am, vol. 80, No. 12, pp. 1745-1757, Dec. 1998.

Yu et al., 'Prevalence and costs of chronic conditions in the VA health care system,' Med Care Res Rev—Supplement, vol. 30, pp. 146S, 2003.

Zhao et al., 'Human bone marrow stem cells exhibit neural phenotypes and ameliorate neurological deficits after grafting into the ischemic brain of rats,' Experimental Neurology, vol. 174, pp. 11-20, 2002.

* cited by examiner

Compressive tissue modulus was positively correlated with volume fraction for all demineralized cancellous bone groups.

COMPOSITIONS AND METHODS FOR REPAIR OR REGENERATION OF SOFT TISSUE

CROSS-REFERENCE TO RELATED APPLICATIONS

This application claims the benefit of priority to U.S. Provisional Application No. 61/560,684, filed Nov. 16, 2011, which incorporated by reference in its entirety.

STATEMENT REGARDING FEDERALLY SPONSORED RESEARCH

Not applicable.

BACKGROUND OF THE INVENTION

Repair of soft tissue damage resulting from injury or disease presents an important medical challenge. The ability to regenerate organs in whole or part would advance treatment of diseases such as liver disease, kidney disease, and diabetes. Repair or replacement of soft tissue would also be useful in repairing or replacing heart valves, blood vessel valves, and in repairing ligaments and tendons. Reconstructive and cosmetic surgery would also be advanced by the ability to generate soft connective tissues and adipose tissue.

Tissue engineering has long sought to develop replacement tissues for patients suffering from organ failure, often utilizing embryonic or adult stem cells as agents of tissue repair or regeneration. Unfortunately, there have been numerous demonstrations that simply injecting stem cells, even those that have been differentiated in vitro, is insufficient. Successful tissue regeneration requires the ability to promote integration with the host and to direct the tissue growth and cell differentiation, processes that depend largely on the transport characteristics of the graft as demonstrated by Hui et al. (Journal of Biomechanics 1996; 29(1):123-132).

Three dimensional scaffolds such as collagen-based hydrogels or poly-lactic-co-glycolic acid (PLGA)-based polymer foams, have demonstrated considerable potential, but the long-term outcomes of therapies employing these scaffolds are far from satisfactory. Collagen hydrogels are contracted by resident cells as much as 90%, making it extremely difficult to promote integration with the host tissue and to generate the necessary tissue mass for organ regeneration. In addition, as hydrogels contract, they exhibit a 100-1000 fold decrease in permeability which limits their ability to transport nutrients and waste products through the implant. The primary limitation of PLGA foams is that they degrade through an autocatalytic process into acidic by-products that are technically biocompatible, but substantially lower the pH within the tissue and often lead to cyst formation. Additional challenges posed by various formulations of PLGA include low mechanical strength relative to most tissues and a surprisingly low permeability compared to structures with similar porosities.

There remains a need in the art for compositions and methods for regenerating damaged or diseased soft tissue.

BRIEF SUMMARY

In certain embodiments, the present invention provides a biocompatible scaffold made from demineralized cancellous bone that has been treated to inhibit osteoinductivity. The demineralized cancellous bone includes a region in which the collagen of the demineralized bone is stiffened. The region of demineralized bone may be stiffened by crosslinking or by physicochemically, including, but not limited to, by heating or stretching, i.e., strain hardening. The biocompatible scaffold is substantially free of mineralized bone.

In certain embodiments the bone is cancellous or cortico-cancellous bone. In certain embodiments the biocompatible scaffold is machined to match, approximate, or be compatible with the shape of a soft tissue or a soft tissue defect.

In certain embodiments, there is variation in the degree or type of crosslinking of the collagen within the crosslinked region. In certain embodiments, crosslinking is relatively low in the portion of the crosslinked region proximal to the interface between the uncrosslinked and crosslinked regions, and increases continuously or discontinuously in portions of the crosslinked region distal to the interface between the crosslinked and uncrosslinked regions.

In certain embodiments, in the region of the biocompatible scaffold containing crosslinked demineralized bone has increased mechanical strength and/or increased resistance to degradation, e.g., enzymatic degradation, relative to the region containing uncrosslinked demineralized bone. In certain embodiments the at least one region comprising crosslinked demineralized bone does not exhibit cell attachment that is substantially different relative to the cell attachment to the at least one region comprising contiguous uncrosslinked demineralized bone. In certain embodiments the at least one region comprising crosslinked demineralized bone exhibits altered cell attachment, e.g. increased or decreased, relative to the cell attachment to the at least one region comprising contiguous uncrosslinked demineralized bone.

In certain embodiments of the above described biocompatible scaffold, at least some portion of the scaffold, including at least some of the pores, contain a hydrogel. In certain further embodiments the hydrogel contains biomolecules. In certain other embodiments of the above described biocompatible scaffold, least some portion of the scaffold, including at least some of the pores, contain a polymer. In certain further embodiments the polymer comprises biomolecules. In certain other embodiments of the above described biocompatible scaffold, the scaffold comprises surface chemistry that includes covalently attached biomolecules and/or adsorbed biomolecules. In certain other embodiments of the above described biocompatible scaffold, the scaffold comprises a surface that has acquired texture, roughness, or three-dimensional unevenness by chemical etching and/or physical etching and/or laser etching. In certain other embodiments of the above described biocompatible scaffold, some or all regions are encapsulated by a biocompatible layer. In certain further embodiments the biocompatible layer is semipermeable and/or bioresorbable.

Turning to another embodiment, there is provided a method for repairing or regenerating soft tissue comprising implanting in the soft tissue in need of repair or regeneration, any of the herein described biocompatible scaffolds. In certain embodiments, the soft tissue comprises organ tissue, e.g., liver tissue.

It is an advantage that a bioscaffold according to the present invention can be designed to have features and performance characteristics suitable for the particular application(s) in which the bioscaffold will be used, including, for example, permeability needed for fluid transport, strength, flexibility, cell attachment, shape retention, porosity, connectivity, and the like.

These and other aspects and embodiments of the herein described invention will be evident upon reference to the following detailed description and attached drawings. All of the U.S. patents, U.S. patent application publications, U.S. patent applications, foreign patents, foreign patent applications and non-patent publications referred to in this specification and/or listed in the Application Data Sheet are incorporated herein by reference in their entirety, as if each was incorporated individually. Aspects and embodiments of the invention can be modified, if necessary, to employ concepts of the various patents, applications and publications to provide yet further embodiments.

DETAILED DESCRIPTION

Figure 1:
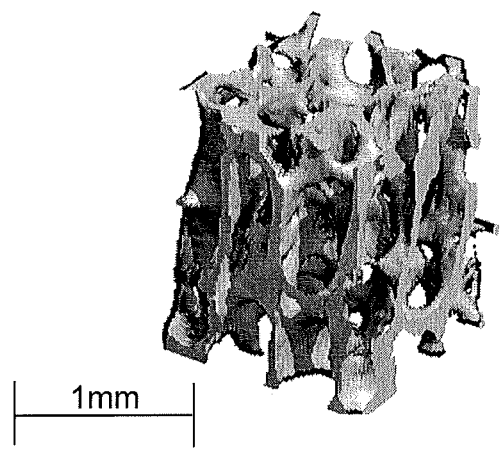
FIG. 1 shows MicroCT images of vertebral (top), pelvic (middle) and femoral (bottom) porcine cancellous bone.
Figure 1:
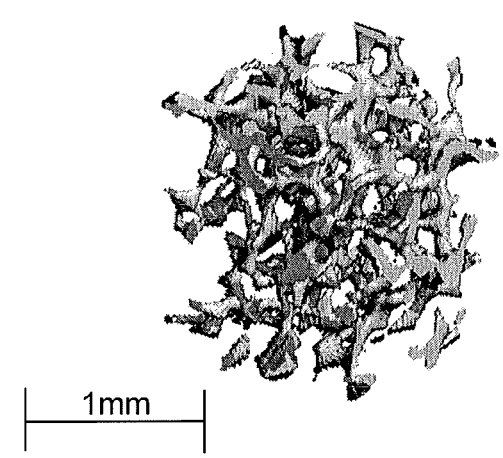
Figure 1:
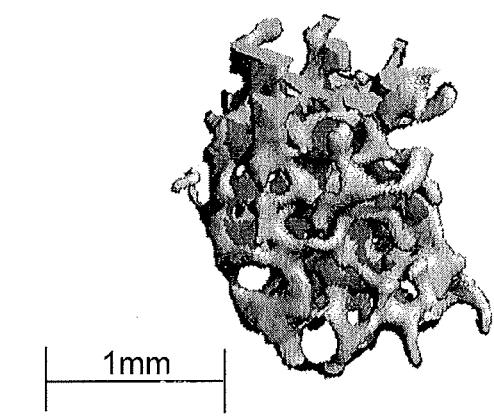

The present disclosure provides biocompatible scaffolds for soft tissue regeneration. In this regard, the present disclosure provides a unique bioscaffold that comprises a collagen-based porous network capable of guiding tissue differentiation that can be used to regrow damaged soft tissues. Its relatively high porosity allows host integration, regeneration of relatively large sections of tissue, and vascularization. The collagen-based porous structure allows binding of a variety of factors to the trabeculae. Hydrogels or similar extracellular matrix material, a variety of biological components and therapeutic compounds may be integrated within the scaffold. The scaffolds contain collagen trabeculae that prevent the scaffold from contracting, thereby allowing the structure to maintain a pre-defined shape and maintain nutrient transport. This is a distinct advantage over other scaffolds and matrices that can contract as much as 60-90%, which reduces transport of nutrients and waste into and out of the scaffold.

In order successfully to repair or rebuild damaged soft tissue, the scaffold desirably provides mechanical integrity, nutrient transport during tissue regeneration, differentiation of well-defined cell populations, vascularization.

Regeneration of tissue such as liver tissue regeneration requires a combined approach with a mechanically competent, relatively highly porous scaffold as the foundation. The porous scaffold is preferably capable of supporting cell migration, e.g., hepatocyte migration and/or cell differentiation as well as sinusoid formation through the expression of extracellular matrix-derived signals and controlled growth factor delivery.

The biocompatible scaffolds described herein are constructed of demineralized bone. The demineralized bone may be cancellous or corticocancellous bone. Cortical bone is the dense surface layer of the bone having little vascularization. In contrast, cancellous bone is a spongy material that makes up the bulk of the interior of bones. Compared to cortical bone it has a low density and strength, but very high surface area. These differences result in demineralized bone having differing properties, with demineralized cancellous bone comprising pores with diameters of about 100 microns to 2 mm while, in contrast, demineralized cortical bone may have a maximum pore size on the order of about 10 nm to 50 microns.

The term "biocompatible" is intended to refer to any material having a relatively low risk of provoking an adverse response when introduced in a mammal, in particular a human patient. For example, a suitable biocompatible material when introduced into a human patient has relatively low immunogenicity and toxicity.

The term "demineralized" refers to bone from which a substantial portion of minerals natively associated with the bone minerals have been removed. The term "demineralized bone" is intended to refer to any bone, including cortical and/or cancellous bone, from any source including autologous, allogeneic and/or xenogeneic bone, that has been demineralized to contain, in certain embodiments, less than about 5 wt % residual calcium, less than about 4 wt % residual calcium, less than about 3 wt % residual calcium, less than about 2 wt % residual calcium, or less than about 1 wt % residual calcium.

By bioscaffolds that are "substantially free of mineralized bone" it is meant that all of the bone within the bioscaffold has been exposed to demineralizing conditions and is at least partially demineralized. Bioscaffolds that are substantially free of mineralized bone are structurally and functionally distinct from bioscaffolds made from bone that has been masked prior to demineralization, as described in US Published Application 20110066241.

The term "osteoconductive" refers to the ability of a substance to support or conduct bone growth, while "osteoinductive" refers to the ability of a substance to induce bone growth.

The porous biocompatible scaffolds described herein may be comprised of demineralized cancellous bone segments and segments of demineralized cancellous bone that have been stiffened by physicochemical methods, such as heating or stretching (i.e., strain hardening), or by crosslinking (e.g., chemically and/or physically) to increase their strength, e.g., to hold sutures, to aid in retention of shape, and/or to resist compression. Unlike other bone matrix scaffolds, the scaffolds described herein are comprised of demineralized bone and do not comprise regions of mineralized bone.

The cancellous bone scaffold as described herein may in certain embodiments be an autograft, an allograft or a xenograft. If the scaffold is a xenograft it may be from, by way of non-limiting example, ovine, porcine or bovine bone. The cancellous bone may be taken from any bone having suitable properties for the intended application of the scaffold. Properties to consider in selecting bone for the bioscaffold include porosity, pore size, connectivity, mechanical strength, surface area/volume ratio, the size of the scaffold required in the application, and the like. In certain embodiments, the cancellous bone is vertebral, femoral, or pelvic cancellous bone. In certain embodiments, the scaffold may be made from a continuous piece of bone. In certain embodiments, the scaffold may be formed from multiple pieces of demineralized bone joined together, for example, by suturing or crosslinking. After a section of bone for use as a bioscaffold has been obtained from cancellous bone, the section of bone is treated to remove marrow. The section of cancellous bone may then be shaped using methods known in the art. Alternatively, the cancellous bone may be shaped before removal of the marrow. The cancellous bone section may be shaped into any shape desired for the scaffold. It will be appreciated that the shape of the scaffold will depend on the application and where in the body the scaffold will be placed.

Non-limiting examples of scaffold shapes may be a sheet, a lobe, a rectangular block, a cylinder, or a dog-bone shape. Although these shapes are given as examples, it is well within the knowledge of the skilled artisan to design any shaped scaffold necessary without undue experimentation. The scaffolds described herein may be flat, tubular, or of complex geometry. The shape of the scaffold will be decided by its intended use. Thus, when forming the scaffold, it may be fashioned to accommodate the desired shape.

The scaffold can be implanted to repair, augment, or replace diseased or damaged organs as described further herein, such as abdominal wall defects, pericardium, hernias, and various other organs and structures including, but not limited to, bone, periosteum, perichondrium, intervertebral disc, articular cartilage, dermis, epidermis, bowel, ligaments, and tendons. In addition, the scaffold may take the form of a tissue repair fabric that can be used as a vascular or intracardiac patch, or as a replacement heart valve. Flat scaffolds may be used, for example, to support prolapsed or hypermobile organs by using the flat scaffold sheet as a sling for the organs. This sling can support organs such as bladder or uterus. Tubular scaffold grafts may be used, for example, to replace cross sections of tubular organs such as esophagus, trachea, intestine, and fallopian tubes. These organs have a basic tubular shape with an outer surface and a luminal surface. In addition, flat sheets and tubular structures can be formed together to form a complex structure to replace or augment cardiac or venous valves.

The size of the scaffold may also vary according to the desired use of the scaffold. In an illustrative embodiment, the scaffold may have a thickness of about 0.1 mm to about 15 mm or about 0.5 mm to about 10 mm, although it may be smaller or larger as required. If the scaffold is being used to repair the liver, the scaffold may be shaped to match the remaining endogenous liver.

In certain embodiments, the structure of the scaffold is a cylindrical-shaped or elliptically-shaped scaffold or a scaffold with a high aspect ratio (i.e., ratio of length to width). In one embodiment, the aspect ratio is greater than 1, and more preferably it is greater than 2 and less than 100. In certain embodiments, the scaffold has a diameter or width in the range of about 3 mm and 12 mm, or between about 4 mm and 10 mm. In certain embodiments, the scaffold is about 7 mm in diameter and about 10 mm in length. In other embodiments, the scaffold is between about 5 and 8 mm in diameter and is between about 8 and 12 mm in length. In another embodiment, the scaffold is about 4, 5, 6, 7, 8, 9, or 10 mm in diameter and is about 8, 9, 10, 11, 12, 13, 14, or 15 mm in length.

It will be appreciated that the cancellous bone scaffold of the present invention may be appropriately fashioned for a wide diversity of applications and the appropriate size can be determined by the skilled person.

The fully demineralized bone may be formed by any method known in the art. In certain embodiments, a mill, such as a CNC mill (CNC Jr. Table Top Milling Machine, CNC Masters, Azusa, Calif.) is used to machine a particular desired shape. Machining of the bone can be carried out before or after demineralization.

It is well known how to prepare fully demineralized bone by a variety of procedures and any of those methods may be used. Illustrative methods include any one or more of the following procedures: decalcification by acid extraction; sonication in detergent solution (e.g., TERGAZYME®, Alconox, White Plains, N.Y.); alternated with rinsing in pure water (as would be understood by the skilled artisan, this cycle may be repeated as needed until substantially all fat, marrow, and other components in the trabecular space are removed); treatment with alkylammonium salts of EDTA, defatting by soaking in acetone; treatment with hydrochloric acid (HCl), in certain embodiments with ethylene diamine tetraacetic acid (EDTA). In certain embodiments, the demineralization process may include treatment with one or more nonionic detergents, such as TRITON® X-100, Tween® 80, N,N-Dimethyldodecylamino-N-oxide, Octylglucoside, Polyoxyethylene (PEG) alcohols, Polyoxyethylene-p-t-octylphenol, Polyoxyethylene nonylphenol, Polyoxyethylene sorbitol esters, Polyoxy-propylene-polyoxyethylene esters, and p-isoOctylpolyoxy-ethylene-phenol formaldehyde polymer.

In certain embodiments, bone scaffolds are washed in peroxide (e.g., $H_2O_2$) to remove osteoinductive factors. Other methods and reagents for removing osteoinductive factors are known in the art, and include those described in U.S. Pub. 2005/0136124. Osteoinductivity of resulting scaffolds can be determined using standard methods in the art, such as ELISA for BMP or other factors that contribute to osteoinductive activity (e.g., fibroblast growth factor-2 (FGF-2), insulin-like growth factor-I and -II (IGF-I and IGF-II), platelet derived growth factor (PDGF), and transforming growth factor-beta 1 (TGF-β1)), on eluates during/after the treatment process.

Stiffening of a region of demineralized cancellous bone provides greater mechanical strength and/or increased resistance to proteolytic enzyme degradation, increasing the in vivo lifetime of the cancellous bone scaffolds. Stiffening may be accomplished by any suitable method, including, for example, by crosslinking or by physicochemical treatments, including, but not limited to, heating or stretching, i.e., strain hardening. The cancellous bone scaffolds may be crosslinked either chemically or mechanically. Crosslinking the cancellous bone scaffold may substantially increase the mechanical integrity of the scaffold, without substantially altering the cytocompatibility of the scaffold. Additionally, both the physical and chemical crosslinking methods may be biologically compatible. Non-limiting examples of physical crosslinking may include dehydrothermal crosslinking or crosslinking by exposure to gamma radiation or to photooxidative crosslinking agents, such as UV-light. Physical crosslinking methods of the cancellous bone scaffolds are well known in the art.

Alternatively, the cancellous bone scaffold may be chemically crosslinked. Functional groups that specifically react with amines may include, but are not limited to, aldehydes, N-hydroxysuccinimide (NHS), isocyanate, epoxide and acrylate. The collagen material of the cancellous bone scaffold is known to comprise lysine residues that may be crosslinked. Functional groups that are non-selective may include, but are not limited to, active esters, epoxides, azides, carbonylimidazole, nitrophenyl carbonates, tresylate, mesylate, tosylate and isocyanate. Other agents may also be employed for chemically crosslinking the cancellous bone scaffold, including, but not limited to, glycosaminoglycan complexing, carbodiimides, genipin, aldehydes such as glutaraldehyde and formaldehyde, acyl azide, poly-epoxy compounds, butanediol diglycidyl ether, ethylene glycol diglycidyl ether, dye mediated photooxidation or tannic acid. Other illustrative crosslinking agents include, but are not limited to, chemical crosslinking agents such as transglutaminase and nitroalcohol.

Other illustrative crosslinking agents include, but are not limited to, 1-ethyl-3-[3-dimethylaminopropyl]carbodiimide hydrochloride (EDC or EDAC). Carbodiimide crosslinkers activate carboxyl groups for spontaneous reaction with primary amines, enabling peptide immobilization and hapten-carrier protein conjugation. 1-ethyl-3-[3-dimethylaminopropyl]carbodiimide hydrochloride (EDC or EDAC) is a commercially available zero-length crosslinking agent used to couple carboxyl groups to primary amines. This crosslinker has been used in diverse applications and reacts with a carboxyl to form an amine-reactive O-acylisourea intermediate. If this intermediate does not encounter an amine, it will hydrolyze and regenerate the carboxyl group. In the presence of N-hydroxysulfosuccinimide (Sulfo-NHS), EDC can be used to convert carboxyl groups to amine-reactive Sulfo-NHS esters. This is accomplished by mixing the EDC with a carboxyl containing molecule and adding Sulfo-NHS.

A combination of different crosslinking agents may be used. The choice of crosslinking agent may depend on the amount of crosslinking desired, although this may also be controlled by controlling the time of the crosslinking reaction and/or by controlling the concentration of the crosslinking agent. It will be appreciated that the mechanical properties of the cancellous bone scaffold may be tailored specifically for a given application by altering crosslinking conditions, including length of reaction time, temperature, and chemical reaction mixture concentrations. In this manner, in certain embodiments, the scaffolds described herein comprise one or more transition regions in which the level or degree of crosslinking gradually (e.g., in a substantially continuous manner) increases (e.g., in a statistically significant manner) or gradually decreases (e.g., in a statistically significant manner) over the region. For example, in a transition region there may exist, along a linear axis or radially, a gradient in which a first level of crosslinking at a first locale is detectably lower than a second level of crosslinking at a second locale, with a substantially continuous increase in the levels or degree of crosslinking directionally along the linear or radial axis at locales therebetween.

In certain embodiments, the scaffolds described herein comprise regions of increased (e.g., in a statistically significant manner) mechanical strength relative to uncrosslinked regions. In this regard, any statistically significant increase in mechanical strength in a crosslinked region relative to uncrosslinked regions is contemplated in the scaffolds described herein. The mechanical properties of the crosslinked scaffold can be evaluated or measured using methods known in the art and described herein, such as by evaluating tension, compression, and suture pull-out strength. The mechanical strength properties of the scaffold will vary depending on the site of implant.

In certain embodiments, the bioscaffold is crosslinked and has a tensile modulus that is at least about 1.5 times greater than that of an uncrosslinked bioscaffold. In certain embodiments, the crosslinked bioscaffold has a tensile modulus that is from about 1.5-4 times greater than that of an uncrosslinked bioscaffold.

In certain embodiments, the bioscaffold is crosslinked and has a compressive modulus that is greater than that of an uncrosslinked bioscaffold. In certain embodiments, the crosslinked bioscaffold has a compressive modulus that is from about 5 times greater than that of an uncrosslinked bioscaffold.

In certain embodiments, the bioscaffold is crosslinked and has an ultimate tensile strength that is greater than greater than that of an uncrosslinked bioscaffold. In certain embodiments, the crosslinked bioscaffold has an ultimate tensile strength that is in the range of from about 5- to about 10 times greater than that of an uncrosslinked bioscaffold.

In certain embodiments, the bioscaffold is crosslinked and has an enzymatic resistance that is greater than that of an uncrosslinked bioscaffold. In certain embodiments, the crosslinked bioscaffold has an enzymatic resistance that is about 3 times greater than the enzymatic resistance of an uncrosslinked bioscaffold.

In certain embodiments, the bioscaffold has a porosity of at least 60%. Suitably, the porosity may be in a range of from about 60% to about 80%. In certain embodiments, the bioscaffold has a connectivity in the range of from about $10/m^2$ to about $20/m^2$. In certain embodiments, the bioscaffold has a permeability in the range of from about $0.1 \times 10^{-9}$ to about $1.5 \times 10^{-9}$ $m^2$.

Strength testing (e.g., tensile strength; elastic modulus) of the scaffolds can be carried out using commercially available measurement devices and known methods (see for example, Beer, et al., (2009). *Mechanics of Materials*. McGraw Hill). In certain embodiments, a suture retention test may be carried out using commercially available force measurement devices, such as CHATTILION™ devices (AMETEK, Inc., Berwyn, Pa.). The average suture breaks between 400-500 g of force; a typical surgeon's pull tends to be 150 g of force. Weld/material strength test may be performed, for example, using a mechanical testing system MTS™ (Eden Prairie, Minn.) to determine the ultimate tensile strength (UTS) of a scaffold.

The term "suturable" means that the mechanical properties of the scaffold include suture retention which permits needles and suture materials to pass through the scaffold material at the time of suturing of the scaffold to sections of native tissue, a process known as anastomosis. During suturing, such scaffold should be resistant to tearing as a result of the tensile forces applied to them by the suture, and should also be resistant to tearing when the suture is knotted. Suturability of tissue repair scaffold, i.e., the ability of scaffold to resist tearing while being sutured, is related to the intrinsic mechanical strength of the scaffold material, the thickness of the graft, the tension applied to the suture, and the rate at which the knot is pulled closed.

In certain embodiments, the scaffolds described herein comprise crosslinked regions having increased enzymatic resistance as compared to uncrosslinked regions. In this regard, any statistically significant increase in enzymatic resistance in a crosslinked region relative to uncrosslinked regions is contemplated in the scaffolds described herein. Enzymatic resistance can be measured using techniques known in the art, for example by culturing, incubating, or otherwise contacting the scaffold with an appropriate enzyme (such as enzymes known to be present in a particular target tissue of interest) under conditions and for a time sufficient for enzyme activity to manifest, and measuring degradation of the crosslinked regions of the scaffold as compared to the uncrosslinked regions, and/or using other appropriate controls.

In certain embodiments, the scaffolds described herein comprise crosslinked regions having altered cell attachment properties as compared to uncrosslinked regions. In this regard, any statistically significant increase or decrease in cell attachment in a crosslinked region relative to uncrosslinked regions is contemplated in the scaffolds described herein. In one embodiment, crosslinking does not affect cell attachment. Thus, the scaffolds described herein may comprise crosslinked regions in which cell attachment thereto is not significantly altered as compared to uncrosslinked regions of the scaffold. Cell attachment can be measured using techniques known in the art, for example by culturing, incubating, or otherwise contacting the scaffold with cells of interest (e.g., liver cells) for an appropriate time and under conditions to allow cell attachment to, or infiltration into, the scaffold, and subsequently measuring cells attached to the scaffold (see also the Examples).

Demineralized cancellous bone is osteoinductive and is most often employed to help promote the regeneration of bone. For utilization in soft tissue repair, however, the osteoinductivity may be removed from the cancellous bone scaffold. Methods are known in the art for removing the osteoinductivity and include, but are not limited to, peroxide (e.g., $H_2O_2$) treatment.

Certain embodiments provide cancellous bone scaffolds where the crosslinked regions may be positioned as desired depending on the application, shape of the scaffold, the site of implant, tissue type and/or shape/size of injury in the tissue. The crosslinked regions may be positioned on one or both ends of a cylindrical or rectangle scaffold, on the outer edges/rim of a scaffold (e.g., for a sheet scaffold), or in the middle of a scaffold. In certain embodiments, the present scaffolds may comprise more than one crosslinked region, alternating with regions of uncrosslinked demineralized bone. There may be any number of crosslinked or uncrosslinked regions as needed for a given application, such as 1, 2, 3, 4, 5, 6, 7, 8, 9, or more regions of crosslinked demineralized bone and 1, 2, 3, 4, 5, 6, 7, 8, 9, 10, or more regions of uncrosslinked demineralized bone for each scaffold. The crosslinked and uncrosslinked regions can be the same size or may be of different sizes, where the crosslinked region may be larger or smaller than the uncrosslinked regions, or vice versa.

As noted, in certain embodiments, the scaffolds described herein may comprise one or more transition regions in which the level of crosslinking gradually increases or gradually decreases. There may be any number of such transition regions as needed, such as 1, 2, 3, 4, 5, 6, 7, 8, 9, or more transition regions.

In certain embodiments, the scaffolds described herein comprise crosslinked regions that allow structural strength for suturing the scaffold. In certain embodiments the bioscaffold may be at least partially covered or wrapped in an epithelial like covering. Nonlimiting examples of suitable epithelial like coverings include small intestine submucosa (SIS) or peritoneum derived from autograft, allograft, or xenograft. Another example includes a thin layer of collagen, e.g., derived from demineralized cortical bone. Another suitable coating could be formed by dipping the scaffold in blood, for example, the patient's own blood, to form a layer of tissue on the scaffold. In certain embodiments, however, the scaffolds described herein may be wrapped in small intestine submucosa (SIS), in addition to or as an alternative to having one or more crosslinked region. SIS is a biocompatible, acellular, collagen matrix and attracts local host cells to infiltrate and replace its substance. SIS can also allow for effective suturing. The SIS for use herein may be autologous, allogeneic or xenogeneic and may be derived from any appropriate source, such as human or pig. Thus, in certain embodiments, the scaffolds described herein may comprise only uncrosslinked demineralized bone and such a scaffold may be wrapped in SIS suitable for suturing. Alternatively, in certain embodiments, the scaffold may comprise a combination of one or more crosslinked regions and may also be wrapped in SIS suitable for suturing. These and related embodiments are contemplated by which the herein described scaffolds may form, or may lead to the generation of, an interface with surrounding tissue, as may in certain further embodiments promote cell and/or tissue ingrowth and/or other generation of cohesive tissue structures. For instance, the scaffold may be wrapped with or chemically bound to one or more of SIS, autograft tissue, allograft tissue, and xenograft tissue (e.g., tendon or ligament or other connective tissue), which may be configured as a thin membranous wrapping of all or part of the scaffold.

In addition, the scaffolds can be designed to allow for sustained release of cells seeded within the scaffolds, or of cytokines or other active agent. In certain embodiments, the scaffolds of the present invention are flexible and may be described as a semisolid scaffold that is permeable to substances such as liquid-dissolved inorganic salts, aqueous fluids and dissolved gaseous agents including oxygen.

In some embodiments, the cancellous bone scaffold may be embedded with, injected with or otherwise have attached thereto, cells, any of a variety of pharmaceuticals, antibiotics, growth factors, hydrogel, collagen gel or mixtures thereof. It is contemplated that any composition, compound or biologic that helps in healing and integration of the scaffold may be added.

Non-limiting examples of cells that may be added to a scaffold include any variety of stem cell, such as adult stem cells or cells derived from the soft tissue to be repaired (e.g., cells from liver, pancreas, skin, bladder, kidney, endothelial cells, or other soft tissue including tendon, ligament, fascia, fibrous tissues, fat, synovial membranes, muscles, nerves, blood vessels, cartilage tissue, meniscal tissue, ligament tissue, tendon tissue, skin tissue, muscle tissue, periosteal tissue, pericardial tissue, synovial tissue, bone marrow, spleen tissue, intervertebral disc tissue, embryonic tissue, periodontal tissue, vascular tissue, blood and combinations thereof) or mixtures thereof. The tissue used can be autogeneic tissue, allogeneic tissue, or xenogeneic tissue.

Non-limiting examples of adult stem cells are hematopoietic stem cells, bone marrow stem cells (e.g., bone marrow stromal cells, (BMSCs) an adult stem cell population), adipose-derived stem cells, and mesenchymal stem cells. In certain embodiments, umbilical cord blood-derived stem cells may also be used. In further embodiments, induced pluripotent stem cells may be used. In one embodiment, endothelial cells are seeded into the scaffold.

Tissue and/or cells can be obtained using any of a variety of conventional techniques, for example, by biopsy or other surgical removal. Preferably, the tissue sample is obtained under aseptic conditions. Once a sample of living tissue has been obtained, the sample can then be processed under sterile conditions to create a suspension of desired cells. In certain embodiments, minced tissue particles can used directly. The particle size of each tissue fragment can vary, for example, the tissue size can be in the range of about 0.1 to 3 $mm^3$, in the range of about 0.5 to 1 $mm^3$, in the range of about 1 to 2 $mm^3$, or in the range of about 2 to 3 $mm^3$.

In one embodiment, the minced tissue has at least one viable cell that can migrate from the tissue fragment onto the scaffold. More preferably, the tissue contains an effective amount of cells that can migrate from the tissue fragment and begin populating the scaffold. In an optional embodiment, the minced tissue fragments may be contacted with a matrix-digesting enzyme to facilitate cell migration out of the extracellular matrix surrounding the cells. The enzymes are used to increase the rate of cell migration out of the extracellular matrix and into the scaffold material. Suitable matrix-digesting enzymes that can be used include, but are not limited to, collagenase, chondroitinase, trypsin, elastase, hyaluronidase, peptidase, thermolysin and protease.

In one embodiment, the minced tissue particles can be formed as a suspension in which the tissue particles are associated with a physiological buffering solution. Suitable physiological buffering solutions include, but are not limited to, saline, phosphate buffer solution, Hank's balanced salts, Tris buffered saline, Hepes buffered saline and combinations thereof. In addition, the tissue can be minced in any standard cell culture medium known to those having ordinary skill in the art, either in the presence or absence of serum. Prior to depositing the suspension of minced tissue on the scaffold or at the site of tissue injury, the minced tissue suspension can be filtered and concentrated, such that only a small quantity of physiological buffering solution remains in the suspension to prevent the tissue particles from drying out, and the minced tissue particles can be directly applied to the scaffold or site of injury. Preferably, the minced tissue particles are loaded at a concentration in the range of approximately 1 to 100 mg/cm$^2$, and more preferably in the range of about 1 to 20 mg/cm$^2$.

The suspension of minced living tissue can be used to as described herein by depositing the suspension of living tissue upon a biocompatible scaffold, such that the tissue and the scaffold become associated. Preferably, the tissue is associated with at least a portion of the scaffold. The scaffold can be implanted in a subject immediately, or alternatively, the construct can be incubated under sterile conditions for a duration and under conditions that are effective to maintain the viability of the tissue sample. In embodiments where the scaffold is incubated, the incubation conditions can vary, but preferably, the scaffold is incubated for a duration in the range of 1 hour to 6 weeks, and more preferably between about 1 week and 6 weeks, at a temperature in the range of about 20 to 40° C., and in an atmosphere containing between about 5 and 10% carbon dioxide ($CO_2$) and high humidity, e.g., approximately 100% humidity.

The levels of nutrient transport and differentiation factors that may be preferred in certain embodiments to maintain stem cell differentiation along the desired lineage can be determined using any method, including those known in the art. Computational and full size experimental models can be constructed for this purpose, varying the placement of nutrient transport pathways in order to optimize the transport properties of the scaffold structure.

In certain embodiments, the cancellous bone scaffold may comprise plasma or platelet rich plasma.

In certain embodiments, the scaffolds described herein have embedded therein, are embedded in, injected with, encapsulated by or otherwise attached to one or more gels, hydrogel, collagen gel, extracellular matrix gels, or other appropriate matrices, or mixtures thereof. In this regard, "hydrogel" is not to be considered as limited to gels which contain water, but extends generally to all hydrophilic gels and gel composites, including those containing organic non-polymeric components in the absence of water. A gel is a state of matter that is intermediate between solids and liquids, and which exists as a solvent inside a solid or semisolid three dimensional network. The density of gels, such as collagen gels, can be optimized using routine methodologies and can vary from, for example, about 0.5 mg/ml to 10 mg/ml of collagen, or higher. In some embodiments, the density of a gel can be about 1, 2, 3, 4, 5, 6, 7, 8, 9, 10, 11, 12, 13, 14, or 15 mg/ml collagen. Illustrative gels include hydrogel, collagen gel, extracellular matrix gels, and the like. In certain embodiments, the scaffolds may contain a hydrogel comprising extracellular matrix components derived from soft tissue, including soft tissue derived from autograft, allograft, or xenograft tissue.

In one embodiment, the gels for use with the scaffolds described herein are laden with cells, such as cells of the tissue type to be repaired or regenerated (e.g., liver cells, kidney cells, bladder cells) or endothelial cells. Cell types for use with the scaffold are described herein and include, for example, hepatocytes, endothelial cells, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells, or precursors of any of these cell types.

Within further aspects, the present scaffolds have embedded therein, are embedded in, injected with, encapsulated by or otherwise attached to polymeric carriers and/or matrices which may be adapted to contain and release a compound or cell type of interest. In certain embodiments, the carrier containing the compound is a combination with a carbohydrate, protein or polypeptide. Within certain embodiments, the polymeric carrier contains or comprises regions, pockets, or granules of one or more of the compounds. For example, within one embodiment, compounds may be incorporated within a matrix which contains the compound, followed by incorporation of the matrix within the polymeric carrier. A variety of matrices can be utilized in this regard, including for example, carbohydrates and polysaccharides such as starch, cellulose, dextran, methylcellulose, and hyaluronic acid, proteins or polypeptides such as albumin, collagen and gelatin.

In one embodiment, the scaffolds described herein have embedded therein, are embedded in, injected with, dipped in, encapsulated by or otherwise attached to a biocompatible layer. Such biocompatible layers may be semipermeable or bioresorbable. In other embodiments, scaffolds may be embedded in or encapsulated by a biodegradable layer. Such biocompatible and/or biodegradable layers include biodegradable polymers. For example, in certain embodiments, poly($\epsilon$-caprolactone) (PCL) may be used with the scaffolds described herein. PCL is an aliphatic polyester which can be degraded by hydrolysis under physiological conditions and it is non-toxic and tissue compatible. The degradation of PCL is significantly slower than that of certain polymers and copolymers of lactic and glycolic acids and is therefore suitable for the design of long-term drug delivery systems. Other illustrative biodegradable polymers include, chitosan, heparin, chitosan-heparin complexes, biodegradable polymers, such as poly (DL-lactide-coglycolide) for sustained release delivery after implantation (Emerich, D F et al., 1999, *Cell Transplant*, 8, 47-58) or compositions comprising polybutylcyanoacrylate. In certain embodiments, bioresorbable polycaprolactone/polyglycolic acid (PCL/PGA) polymers are suitable. Examples of other biodegradable polymers include polymers or copolymers formed from monomers of lactide, glycolide, dioxanone, and caprolactone; collagen, fibrin, and silk; poly-(orthoesters) and poly-(anhydrides), polylactic acid, polyglycolic acid, copolymers of polylactic and polyglycolic acid (e.g., poly(lactic-co-glycolic acid; PLGA), polyepsilon caprolactone, polyhydroxy butyric acid, polyorthoesters, polyacetals, polydihydropyrans, polycyanoacrylates and cross linked or amphipathic block copolymers of hydrogels. As used herein, the term "glycolide" is understood to include polyglycolic acid. Further, the term "lactide" is understood to include L-lactide, D-lactide, blends thereof, and lactic acid polymers and copolymers.

Biocompatible layers may be applied to the scaffold, by a variety of well-known techniques. For illustration, heparin can be applied to the scaffold in various ways including: First, benzalkonium heparin (BA-Hep) solution can be applied to the scaffold by dipping the scaffold in the solution and then air-drying it. This procedure treats the scaffold with an ionically bound BA-Hep complex. Second, EDC can be used to activate the heparin, then to covalently bond the heparin to the scaffold. Third, EDC can be used to activate the collagen, then covalently bond protamine to the collagen and then ionically bond heparin to the protamine. Many other coating, bonding, and attachment procedures are well known in the art and may also be used. Treatment of the scaffold with drugs in addition to or in substitution for heparin may be accomplished as described elsewhere herein and based on art-established techniques.

In other embodiments, the scaffolds described herein may employ inert materials such as synthetic silicones, for example, Silastic, silicone rubber or other polymers manufactured, for example, by the Dow-Corning Corporation.

It is also possible to add solids (e.g., barium sulfate) that will render the scaffolds radio opaque. The solids that may be added also include those that will promote tissue regeneration or regrowth, as well as those that act as buffers, reinforcing materials or porosity modifiers.

In other embodiments, the cancellous bone scaffold may be embedded with or otherwise comprise any of a variety of biomolecules, growth factors, differentiation factors, and like biological components. Any agent that facilitates tissue repair is contemplated for use with the scaffolds described herein. The biological components used in the scaffolds can also be selected from among a variety of effectors that, when present at the site of injury, promote healing and/or regeneration of the affected tissue. In addition to being compounds or agents that actually promote or expedite healing, the effectors may also include compounds or agents that prevent infection (e.g., antimicrobial agents and antibiotics), compounds or agents that reduce inflammation (e.g., anti-inflammatory agents), compounds that prevent or minimize adhesion formation, such as oxidized regenerated cellulose (e.g., INTERCEED® and SURGICEL®, available from Ethicon, Inc.), hyaluronic acid, and compounds or agents that suppress the immune system (e.g., immunosuppressants).

By way of example, other types of effectors present within the scaffolds described herein can include heterologous or autologous growth factors, proteins (including matrix proteins), extracellular matrix, devitalized ECM, peptides, antibodies, enzymes, platelets, glycoproteins, hormones, cytokines, glycosaminoglycans, nucleic acids, analgesics, viruses, virus particles, and cell types. It is understood that one or more effectors of the same or different functionality may be incorporated within the scaffold.

In certain embodiments, various cell types can be used as effectors in the scaffolds described herein. Suitable cell types that can serve as effectors include, but are not limited to, osteocytes, osteoblasts, osteoclasts, fibroblasts, stem cells, pluripotent cells, chondrocyte progenitors, chondrocytes, endothelial cells, macrophages, leukocytes, adipocytes, monocytes, plasma cells, mast cells, umbilical cord cells, stromal cells, mesenchymal stem cells, epithelial cells, myoblasts, tenocytes, ligament fibroblasts, neurons, and bone marrow cells. In certain embodiments, cells are embedded in or infused in any of the gels as described herein. Thus, the scaffolds described herein may be, in certain embodiments, infused with cell-laden gels such as collagen gels and the like.

Further biological components/agents for use with the scaffolds described herein include any one or more of a variety of cytokines. By "cytokine" as used herein is meant a generic term for proteins and polypeptides released by one cell population that act on another cell as intercellular mediators. Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatocyte growth factor (HGF); fibroblast growth factor; prolactin; placental lactogen; tumor necrosis factor-alpha and -beta; mullerian-inhibiting substance; mouse gonadotropin-associated peptide; inhibin; activin; vascular endothelial growth factor (VEGF); integrin; thrombopoietin (TPO); nerve growth factors such as NGF-beta; platelet-growth factor; transforming growth factors (TGFs) such as TGF-alpha and TGF-beta; insulin-like growth factor-I and -II; erythropoietin (EPO); osteoinductive factors; interferons such as interferon-alpha, beta, and -gamma; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1alpha, IL-2, IL-3, IL-4, IL-5, IL-6, IL-7, IL-8, IL-9, IL-10, IL-11, IL-12; IL-15, a tumor necrosis factor such as TNF-alpha or TNF-beta; and other polypeptide factors including LIF and kit ligand (KL). As used herein, the term cytokine includes proteins from natural sources or from recombinant cell culture, and biologically active equivalents of the native sequence cytokines.

Suitable agents likewise include the agonists and antagonists of the agents noted above. A cytokine or growth factor can also include combinations of the factors listed above. In addition, the factor can be an autologous factor that is supplied by platelets in the blood. In this case, the growth factor from platelets will be an undefined cocktail of various growth factors.

As used herein, the term "protein" embraces glycoproteins, polypeptides, lipoproteins, proteoglycans, peptides, and fragments thereof, including naturally occurring, recombinantly produced, and chemically synthesized products, and further including analogs and homologs generated using naturally and non-naturally occurring amino acids. Further examples of proteins useful as agents or effectors include, but are not limited to, pleiotrophin, endothelin, tenascin, fibronectin, fibrinogen, vitronectin, V-CAM, I-CAM, N-CAM, selectin, cadherin, integrin, laminin, actin, myosin, collagen, microfilament, intermediate filament, antibody, elastin, fibrillin, and fragments thereof.

Glycosaminoglycans, highly charged polysaccharides which play a role in cellular adhesion, may also be used as agents in the scaffolds described herein. Exemplary glycosaminoglycans useful as effectors include, but are not limited to, heparan sulfate, heparin, chondroitin sulfate, dermatan sulfate, keratan sulfate, hyaluronan (also known as hyaluronic acid), and combinations thereof.

Additional illustrative adhesion agents contemplated for use with the scaffolds herein include hyaluronic acid, fibrin glue, fibrin clot, collagen gel, gelatin-resorcin-formalin adhesive, mussel-based adhesive, dihydroxyphenylalanine (DOPA) based adhesive, chitosan, transglutaminase, poly (amino acid)-based adhesive, cellulose-based adhesive, synthetic acrylate-based adhesives, platelet rich plasma (PRP), MATRIGEL® matrix, Monostearoyl Glycerol co-Succinate (MGSA), Monostearoyl Glycerol co-Succinate/polyethylene glycol (MGSA/PEG) copolymers, laminin, elastin, proteoglycans, and combinations thereof.

The scaffolds described herein can also be used in gene therapy techniques in which nucleic acids, viruses, or virus particles deliver a gene of interest, which encodes at least one gene product of interest, to specific cells or cell types. Accordingly, the biological agent/effector can be a nucleic acid (e.g., DNA, RNA, or an oligonucleotide), a virus, a virus particle, or a non-viral vector. The viruses and virus particles may be, or may be derived from, DNA or RNA viruses. The gene product of interest is preferably selected from the group consisting of proteins, polypeptides, interference ribonucleic acids (iRNA) and combinations thereof.

Once the applicable nucleic acids and/or viral agents (i.e., viruses or viral particles) are incorporated into the biocompatible scaffold, the scaffold can then be implanted into a particular site to elicit a type of biological response. The nucleic acid or viral agent can then be taken up by the cells and any proteins that they encode can be produced locally by the cells. In one embodiment, the nucleic acid or viral agent can be taken up by the cells within the tissue fragment of the minced tissue suspension, or, in an alternative embodiment, the nucleic acid or viral agent can be taken up by the cells in the tissue surrounding the site of the injured tissue. One of ordinary skill in the art will recognize that the protein produced can be a protein of the type noted above, or a similar protein that facilitates an enhanced capacity of the tissue to heal an injury or a disease, combat an infection, or reduce an inflammatory response. Nucleic acids can also be used to block the expression of unwanted gene product that may impact negatively on a tissue repair process or other normal biological processes. DNA, RNA and viral agents are often used to accomplish such an expression blocking function, which is also known as gene expression knock out.

One of ordinary skill in the art will appreciate that the identity of the biological component may be determined by a surgeon, based on principles of medical science and the applicable treatment objectives.

The biological component or effector of the scaffolds described herein can be incorporated within the scaffold before or after manufacture of the scaffold, or before or after the surgical placement of the scaffold.

Prior to surgical placement, the biocompatible scaffold can be placed in a suitable container comprising the biological component. After an appropriate time and under suitable conditions, the scaffold will become impregnated with the biological component. Alternatively, the biological component can be incorporated within the scaffold by, for example, using an appropriately gauged syringe to inject the biological agent(s) into the scaffold. Other methods well known to those of ordinary skill in the art can be applied in order to load a scaffold with an appropriate biological component, such as mixing, pressing, spreading, centrifuging and placing the biological component into the scaffold. Alternatively, the biological component can be mixed with a gel-like carrier prior to injection into the scaffold. The gel-like carrier can be a biological or synthetic hydrogel as described elsewhere herein, and/or may include an alginate, a crosslinked alginate, hyaluronic acid, collagen gel, poly(N-isopropylacrylamide), poly(oxyalkylene), a copolymer of poly(ethylene oxide)-poly(propylene oxide), poly(vinyl alcohol) and blends thereof.

Following surgical placement, an implant wherein the biocompatible scaffold is devoid of any biological component can be infused with biological agent(s), or an implant wherein the scaffold includes at least one biological component can be augmented with a supplemental quantity of the biological component. One method of incorporating a biological component within a surgically installed implant is by injection using an appropriately gauged syringe.

The amount of the biological component included with a biocompatible scaffold will vary depending on a variety of factors, including the size of the scaffold, additional material added to the scaffold (e.g., gels, cells, polymers, etc), the porosity of the scaffold, the identity of the biologically component, and the intended purpose of the tissue repair scaffold. One of ordinary skill in the art can readily determine the appropriate quantity of biological component to include within a biocompatible scaffold for a given application in order to facilitate and/or expedite the healing of tissue. The amount of biological component will, of course, vary depending upon the identity of the biological component and the given application.

Further illustrative effectors or agents for use with the scaffolds described herein include anti-inflammatory agents or drugs such as, but not limited to, steroids and glucocorticoids (including betamethasone, budesonide, dexamethasone, hydrocortisone acetate, hydrocortisone, hydrocortisone, methylprednisolone, prednisolone, prednisone, triamcinolone), nonsteroidal anti-inflammatory drugs (NSAIDS) including aspirin, ibuprofen, naproxen, methotrexate, sulfasalazine, leflunomide, anti-TNF medications, cyclophosphamide and mycophenolate.

Further agents for use with the scaffolds described herein include any one or more of a variety of antibiotics. Antibiotics are well known in the art and include Abacavir, Acyclovir, Albendazole, Amikacin, Amoxicillin, Ampicillin, Azithromycin, Aztreonam, Benzilpenicillin, Cefepime, Ceftriaxone, Cephalexin, Chloramphenicol, Chloroquine, Cilastatin, Clindamycin, Co-trimoxazole, Didanosine, Dioxidine, Doxycycline, Famciclovir, fluoroquinolones, Fluconazole, Fosfomycin, Furazolidone, Fusidic acid, Ganciclovir, Gentamicin, Isoniazid, Josamycin, Kanamycin, Ketoconazole, Lamivudine, Lincomycin, Linezolid, Mebendazole, Meropenem, Metronidazole, Moxifloxacin, Mupirocin, Nystatin, Nitrofurantoin, Nitroxoline, Norfloxacin, Ofloxacin, Ornidazole, Oseltamivir, Polymixin B, Polymyxin M, Proguanil, Ribavirin, Rifampicin, Rimantadine, Roxithromycin, Spectinomycin, Sulfodimidin, Teicoplanin, Terbinafine, Tetracycline, Timidazole, Valaciclovir, Valganciclovir, Vancomycin, Zanamivir, and Zidovudine.

Further agents for use with the scaffolds described herein include any one or more of a variety of anti-viral drugs. Anti-viral drugs are well known in the art. Illustrative anti-viral agents include, but are not limited to Abacavir—anti-HIV. NRTI drug. "Ziagen" (ViiV Healthcare). In combination formulations: "Trizivir" and "Kivexa/Epzicom", Aciclovir—anti-HSV, Acyclovir, Adefovir, Amantadine, Amprenavir, Ampligen, Arbidol, Atazanavir, Atripla, Boceprevir, Cidofovir, Combivir, Darunavir, Delavirdine, Didanosine, Docosanol, Edoxudine, Efavirenz, Emtricitabine, Enfuvirtide, Entecavir, Entry inhibitors, Famciclovir, Fixed dose combination (antiretroviral), Fomivirsen, Fosamprenavir, Foscarnet, Fosfonet, Fusion inhibitor, Ganciclovir, Ibacitabine, Immunovir, Idoxuridine, Imiquimod, Indinavir, Inosine, Integrase inhibitor, Interferon type III, Interferon type II, Interferon type I, Interferon, Lamivudine, Lopinavir, Loviride, Maraviroc, Moroxydine, Methisazone, Nelfinavir, Nevirapine, Nexavir, Nucleoside analogues, Oseltamivir, Peginterferon alfa-2a, Penciclovir, Peramivir, Pleconaril, Podophyllotoxin, Protease inhibitor, Raltegravir, Reverse transcriptase inhibitor, Ribavirin, Rimantadine, Ritonavir, Pyramidine, Saquinavir, Stavudine, Synergistic enhancer (antiretroviral), Tea tree oil, Tenofovir, Tenofovir disoproxil, Tipranavir, Trifluridine, Trizivir, Tromantadine, Truvada, Valaciclovir, Valganciclovir, Vicriviroc, Vidarabine, Viramidine, Zalcitabine, Zanamivir, and Zidovudine.

In further embodiments, the surface chemistry of the scaffold may be altered. In this regard, the surface may be modified by covalent (direct) attachment of biomolecules or by adsorption of biomolecules. Illustrative biomolecules include any of the biomolecules disclosed herein, such as but not limited to cellular proteins, any of the polymers described herein, collagens, extracellular matrix components, cytokines, growth factors, anti-inflammatory mediators and others.

In certain embodiments, the surface structure of the scaffold is modified to provide texture, roughness and/or three-dimensional unevenness to the scaffold. The surface roughness of the scaffold may be altered by chemical etching or by physical etching. Methods for chemical and physical etching are known in the art and include laser-based etching and etching using a Nanojet tool (see e.g., *J. Vac. Sci. Technol. B* 19, 2723 (2001)). In certain embodiments, at least a portion of the bioscaffold is surface etched to form features of about 25 µm.

The scaffolds described herein are used for soft tissue repair. Organ/tissue regeneration is challenging and few technologies have been developed that provide an opportunity to integrate cellular level differentiation strategies, structural mechanics, and fluid transport. The scaffolds described herein provide the distinct advantages of having the ability to (1) encourage differentiation of a well-defined cell population, (2) provide mechanical integrity, (3) encourage nutrient transport as the organ regenerates, and (4) provide easy integration with the large blood vessels.

The bioscaffolds described herein can be used for any soft tissue repair and regeneration. In certain preferred embodiments, the scaffolds described herein may be used to rebuild damaged liver tissue. In certain embodiments, damaged liver tissue is rebuilt in segments by using the soft tissue bioscaffolds described herein to create repeating base structures that can be assembled into the desired size and shape. This allows partial and total replacements and makes it possible to recreate specific blood vessel branching architectures. In certain embodiments, the interior of the scaffold is seeded with bone marrow stromal cells, (BMSCs) an adult stem cell population that can be obtained easily from the patient and differentiated into hepatocytes in vitro prior to implantation. In particular embodiments, the blood vessel attachments are coated with a chitosan-heparin complex in order to prevent coagulation and seeded with endothelial cells to encourage blood vessel development. The resulting structure has the beneficial characteristics of a liver transplant without the risk of rejection, potentially obviating the need for liver organ donation as well as the majority of adverse side effects.

In other contemplated embodiments, the scaffolds described herein may be used to rebuild or regenerate damaged soft tissue such as pancreas, skin, bladder, kidney, tendon, ligament, fascia, fibrous tissues, fat, synovial membranes, muscles, nerves and blood vessels.

The tissue repair scaffolds described herein can be used in a variety of surgical and non-surgical applications. In some surgical applications, such as for use in the repair of a variety of tissues, the scaffolds are desirably capable of being handled in the operating room, and they may preferably be amenable to being sutured or otherwise fastened without tearing. Additionally, in these and related embodiments, the scaffolds preferably have a burst strength that is adequate to reinforce the tissue, and the structure of the scaffold encourages tissue ingrowth. By way of non-limiting example, the scaffolds of the present invention can be highly porous to allow cell growth therein. In certain embodiments, the median pore size is at least about 50 µm, 100 µm or 200 µm. In certain embodiments, the median pore size is in the range of from about 100 to about 2000 µm, or about 200 to 1000 µm. The median pore size may be about 50, 75, 100, 125, 150, 175, 200, 225, 250, 275, 300, 325, 350, 375, 400, 425, 450, 475, 500, 525, 550, 575, 600, 625, 650, 675, 700, 725, 750, 800, 825, 850, 875, 900, 925, 950, 975, 1000, 1025. 1050, 1075, 1100, 1125, 1150, 1175, 1200, 1225, 1250, 1275, 1300, 1325, 1350, 1375, 1400, 1425, 1450, 1475, 1500, 1525, 1550, 1575, 1600, 1625, 1650, 1675, 1700, 1725, 1750, 1775, 1800, 1825, 1850, 1875, 1900, 1925, 1950, 1975, or 2000 µm.

In these embodiments, the scaffold should be sufficiently pliable to accommodate tissue growth within the interior region of the scaffold, so that the geometry of the scaffold can be remodeled as tissue ingrowth increases. Accordingly, tissue can be grown on the surface of the biocompatible scaffold, or alternatively, tissue can be grown into and on the surface of the biocompatible scaffold, such that the tissue becomes embedded in and integrated with the scaffold.

In one embodiment of the present disclosure, the tissue repair scaffold is used in the treatment of a tissue injury such as injury to liver, kidney or pancreas. In certain embodiments, repairing tissue injuries involves the steps of obtaining a sample of living tissue by any of the variety of techniques known to those having ordinary skill in the art (see e.g., U.S. Pat. No. 7,824,701), processing that sample of living tissue under sterile conditions, such as for example by cutting the tissue, to create at least one minced, finely divided tissue particle, depositing the tissue sample upon the biocompatible scaffold, such that the tissue sample becomes associated with the scaffold to form a tissue repair scaffold implant, and placing the tissue repair scaffold in a desired position relative to the tissue injury. Repairing tissue injuries may also involve placing the scaffold at the site of tissue injury and then depositing the fine tissue particles onto the scaffold. The cells in the tissue particles associated with the scaffold can migrate to the scaffold and begin differentiating, proliferating and integrating with surrounding tissue at the site of implantation, thereby repairing the tissue injury. This method for repairing tissue injuries can include one or more additional, optional steps. Prior to the step of placing the tissue repair scaffold in a desired position relative to the tissue injury, for example, the scaffold and associated tissue particles can be incubated for a duration and under conditions effective to allow cells within the tissue particles to migrate from the tissue and begin populating the scaffold.

The minced tissue or cells derived therefrom can then be distributed onto a scaffold using a cell spreader so as to cover the entire scaffold. In one embodiment, the tissue particles can be adhered to the scaffolds using any of the adhesive agents described above, for example, fibrin glue or platelet rich plasma. In embodiments using fibrin glue or platelet rich plasma, a few microliters of thrombin can be placed on the scaffolds, prior to distribution of fibrinogen or platelet rich plasma on the scaffolds, and allowed to set. Once the tissue particles and any additional agents have been deposited on the scaffold, the tissue repair scaffold can then be implanted immediately, or alternatively, the scaffold can be cultured in vitro for a duration and under conditions sufficient to allow the cells in the tissue particles to migrate from the tissue particles onto the scaffold. In other embodiments, the scaffold is cultured in vitro for a duration and under conditions sufficient to allow cells to differentiate from a precursor cell (e.g., a stem cell) into an appropriate cell type (e.g., hepatocyte).

The methods of repairing tissue injuries using the scaffolds described herein can be conducted during a surgical operation to repair the tissue injury. Alternatively, the steps of processing the tissue sample to create minced, finely divided tissue particles, depositing the tissue particles upon the scaffold to form a tissue repair scaffold, and/or incubating the tissue repair scaffold prior to implantation can be conducted at another, sterile location prior to surgical placement of the scaffold relative to the site of injury.

The scaffolds used to repair injured tissue can be of a size and shape such that they match the geometry and dimensions of a desired portion or lesion of the tissue to be treated. The scaffold can be sized and shaped to produce the appropriate geometry by numerous techniques including cutting, folding, rolling, or otherwise manipulating the scaffold. As noted above, the biological component may be added to the scaffold during or after manufacture of the scaffold or before or after the scaffold is installed in a patient. An additional quantity of the biological component may be added after the scaffold is implanted. Once access is made into the affected anatomical site (whether by minimally invasive, open or mini-open surgical technique), the scaffold can be affixed to a desired position relative to the tissue injury, such as within a tear or lesion. Once the scaffold is placed in the desired position or lesion, it can be affixed by using a suitable technique. In one aspect, the scaffold can be affixed by a chemical and/or mechanical fastening technique. Suitable chemical fasteners include glues and/or adhesive such as fibrin glue, fibrin clot, and other known biologically compatible adhesives. Suitable mechanical fasteners include sutures, staples, tissue tacks, suture anchors, darts, screws, pins and arrows. It is understood that combinations of one or more chemical and/or mechanical fasteners can be used. Alternatively, one need not use any chemical and/or mechanical fasteners. Instead, placement of the scaffold can be accomplished through an interference fit of the scaffold with an appropriate site in the tissue to be treated.

The tissue repair scaffold can be utilized in a variety of configurations. For example, the scaffold can be folded or stacked in multiple laminates or it can be rolled into the shape or a tube-like or cylindrical structure. As would be understood by the skilled person, tissues and scaffolds can be joined, for example, by suturing, stapling, clipping, adhering, or anchoring, to ends or other region of the scaffold. In some embodiments, the attachment is at the crosslinked regions of the scaffold.

The scaffolds of the invention can also be used for organ repair replacement or regeneration strategies that may benefit from these unique tissue scaffolds. For example, these scaffolds can be used for spinal disc, cranial tissue, dura, nerve tissue, liver, pancreas, kidney, bladder, uterus, esophagus, liver spleen, cardiac muscle, skeletal muscle, skin, fascia, pelvic floor, stomach, tendons, cartilage, ligaments, and breast tissues.

In yet another embodiment, the scaffolds of the present disclosure can be used to create a biological assay for measuring the effect of a substance on living tissue. In this embodiment, tissue constructs are created, as described above, by providing a biocompatible scaffold as described herein, obtaining a sample of living tissue, processing the sample of living tissue under sterile conditions to form a suspension of minced tissue having minced tissue fragments and a physiological buffering solution, and depositing the suspension of minced tissue on the biocompatible scaffold such that the suspension of minced tissue and the scaffold become associated. The tissue construct is incubated under conditions that are effective to allow cells within the minced tissue to populate the scaffold.

The tissue construct can then be contacted with the substance that is to be tested, and the effect(s) of that substance can be determined. These tissue constructs can be used to determine and/or test the biological responses to a test substance, such as for example, cell viability, growth, migration, differentiation and maintenance of cell phenotype, metabolic activity, induction or repression. These biological responses can be assayed using any of a variety of techniques known to those having skill in the art, for example, proliferation assay, cell migration assay, protein assay, gene expression assay, viability assay, enzyme assay, calorimetric assay or metabolic assay. By way of non-limiting example, the expression of a selected gene(s) or gene products typically expressed by the tissue of the tissue construct, for example, the expression of liver enzymes, type II, type 1x or type XI collagens, may be determined using a variety known assays, for example, northern blot analysis, RNAse protection assays, polymerase chain reaction (PCR), western blot analysis and/or enzyme-linked immunoabsorbant assay (ELISA). Suitable substances that can be tested using the tissue constructs of the present invention include, but are not limited to, drugs, pharmaceutical compositions, chemicals, microbes, elements, cytokines, growth factors, hormones, antibodies, peptides, ligands, antagonists of membrane-bound receptors, and combinations thereof.

Certain embodiments contemplate the development of robust, in vitro models of human toxicity in order to complement, enhance or augment information obtained from in vivo animal studies, and in some instances to provide data of greater relevance to human clinical contexts. Therefore, in certain embodiments, the scaffolds described herein can be used in human toxicology testing by infusing human primary hepatocytes in the scaffold to model processes that occur in the intact liver.

The scaffolds of the present invention can also be used as delivery devices for therapeutics, wherein the therapeutic comprises the minced tissue, which may include a combination of cells, extracellular matrix and/or inherent growth factors. The scaffold portion of the implant may thus permit hormones and proteins to be released into the surrounding environment.

The methods of repairing or regenerating tissue injury or disease using the scaffolds according to the present invention can be conducted during a surgical operation to repair the tissue injury. A patient is prepared for tissue repair surgery in a conventional manner using conventional surgical techniques. Tissue repair is performed at the site of injured tissue using the scaffolds as disclosed herein. If desired, a tissue sample to be used with the scaffolds described herein may be obtained from the patient (or another donor) using appropriate tools and techniques. The tissue sample is finely minced and divided into at least one tissue particle having an appropriate particle size (for example, in the range of about 0.1 to 3 $mm^3$). The tissue can be minced using a conventional mincing technique such as two sterile scalpels used in a parallel direction. An appropriate amount of tissue (such as between about 300 to 500 mg of tissue) is minced in the presence of a physiological buffering solution, depending on the extent of the tissue injury at the site of repair. The minced tissue is filtered and concentrated to separate the minced tissue particle from the physiological buffering solution. The minced tissue can be concentrated using any of a variety of conventional techniques, such as for example, sieving, sedimenting or centrifuging. The minced tissue particles are then distributed using a cell spreader onto a 4×5 cm biocompatible scaffold that has been soaked in Dulbecco's modified Eagles medium (DMEM). An adhesion agent can be added to the biocompatible scaffold and the minced tissue particles. The tissue repair scaffold is implanted at the site of tissue injury, either immediately or after a period of in vitro incubation. Final wound closure is performed in a conventional manner using conventional surgical techniques.

As would be understood by the skilled person, various clinical and physical factors known to the clinician can be used to determine the effectiveness of the scaffolds at regenerating damaged tissue, including histological analysis, tissue/organ functional analyses (e.g., measurement of liver enzymes, glomerular filtration rate (GFR) or serum creatinine levels for kidney function, etc), physical palpation, MRI, PET scan, CAT scan, X-ray, and the like. A variety of animal models, such as mouse, rat, pig and monkey models, are also available for testing the efficacy of the scaffolds described herein.

EXAMPLES

Example 1

Construction of Demineralized Cancellous Bone Bioscaffold

Cancellous bone is harvested from the porcine spines obtained from the Purdue Butcher Block (West Lafayette, Ind.), a USDA-inspected abattoir. Porcine spines are stored at −20° C. until use. After thawing for 24 h at 4° C., the vertebrae of the spine are disarticulated by cutting through the intervertebral disc and spinal ligaments at the facet joints. Residual soft tissues are dissected from the remainder of the vertebrae. Using a CNC mill (CNC Jr. Table Top Milling Machine, CNC Masters, Azusa, Calif.), cylindrical samples of 7 mm in diameter and 10 mm in length are machined. After machining is complete, all structures are alternately sonicated for 4 h in a 1% detergent solution (TERGEZYME® detergent Alconox, White Plains, N.Y.) and rinsed with running nanopure water (MILLIPORE® Corporation, Billerica, Mass.) for 30 minutes. This cycle is repeated until all fat, marrow, and other components in the trabecular space are removed. The structures are then defatted by soaking in acetone for 12 h with a solution change after 6 h, followed by air drying for 24 h. The structures are placed in a demineralizing solution composed of 1.0 M hydrochloric acid (HCl) and 1.9 mM ethylene diamine tetraacetic acid (EDTA) 4.5 h (optimal demineralization time as previously determined). The samples are then air dried. The scaffold is then washed in 3% peroxide for 12 h to remove osteoinductive factors. Further chemical processing divides the specimens into three configurations (Table 1). Collagen crosslinking has been shown to enhance cell attachment. In addition, the collagen remaining after cancellous bone demineralization can provoke a mild immunogenic response in the blood and also has some thrombogenic properties. However, coating the structure with heparin and chitosan in a layer-by-layer process mitigates both issues and further promotes endothelialization (Keuren, Arterioscler Thromb Vasc Biol 2004; 24:613-616).

TABLE 1

Experimental Configurations

| Configuration | Treatments |
|---|---|
| A | Porous collagen scaffold |
| B | Porous collagen scaffold + (1-ethyl-3-(3-dimethyl aminopropyl) carbodiimide (EDC) crosslinking |
| C | Porous collagen scaffold + genipin-based crosslinking |
| D | Porous collagen scaffold + heparin coating |
| E | Porous collagen scaffold + heparin-chitosan layered coating |

Heparin is an anticoagulant, and chitosan plays a critical role in cell attachment and growth. Platelet activation and thrombogenesis are statistically compared using standard assays for scaffolds with and without heparin-chitosan layers as outlined in Table 1. The number of layers is increased until the platelet activation and thrombogenecity reach acceptable levels.

Example 2

Migration of Hepatocytes and Hepatocyte Precursors

Hepatocytes are harvested from freshly sacrificed rat livers and expanded in culture (passaged no more than two times) prior to seeding on cylindrical scaffolds. The scaffolds are pressed to fit into a custom cell culture chamber designed to hold the specimens in place while the cells migrate into the scaffolds. After one week in culture, the scaffolds are fixed in 4% paraformaldehyde/4% sucrose in neutral buffered PBS. The scaffolds are then sectioned longitudinally and washed for no more than five minutes in PBS with 0.1% TRITON® X-100 detergent. The cells are then stained with 2.5 mg/ml Hoechst stain 33258 in PBS and 0.1% TRITON® X-100 detergent for five minutes and the rinse is repeated. The samples are then examined under a fluorescence microscope with a 2 DAPI filter and the penetration distance is quantified. A one factor ANOVA is used to evaluate the effects of the treatment configurations A-E.

Example 3

Differentiation of Hepatocyte Precursors within the Porous Collagen Scaffold Yamamoto et al. demonstrated that a combination of hepatocyte growth factor (HGF), DMSO, and oncostatin M led to hepatocytic differentiation of BMSCs based on phenotypic markers (Yamamoto et al. FEBS Journal 2008; 275:1260-1273). Sellaro et al. later showed that the addition of devitalized liver tissue aids in maintaining differentiation (Sellaro et al. FEBS Journal 2008; 275:1260-1273; Sellaro et al. Tissue Eng 2007; 13(9):2301-10). This Example evaluates each factor and the incorporation of liver-derived extracellular matrix (ECM) in turn. In particular, this Example evaluates the differentiation process in a three dimensional culture comprising a cylindrical demineralized cancellous bone segment impregnated with BMSCs, and a collagen hydrogel with or without the devitalized ECM. It has already been established that the cancellous bone structure eliminates contraction of the collagen and maintains high permeability to nutrients and growth factors. Functional assessment at 7, 14, and 21 days post-differentiation is determined by measuring albumin production and by performing an ammonia challenge (Sellaro et al. FEBS Journal 2008; 275:1260-1273; Sellaro et al. Tissue Eng 2007; 13(9):2301-10).

Example 4

Formation of Sinusoids within a Collagen ECM

In this example and Example 5, the time course of hepatic sinusoid formation using two complementary methods. The first consists of infusing an endothelial cell-laden collagen hydrogel into the porous collagen structure and the second utilizes VEGF-doped PLGA particles to guide the formation of the sinusoids. Without being bound by theory, it is thought that the combined treatment will significantly accelerate the formation of sinusoids lined with hepatic sinusoidal endothelial cells within the porous collagen scaffold.

Invasion of endothelial cells into the porous collagen scaffold is accomplished by infusing a low density (2 mg/ml) collagen hydrogel populated with endothelial cells into the porous collagen matrix. Previous work (e.g., Gentleman et al., 2004 *Tiss. Eng.* 10:421-427) has established that the cancellous bone structure eliminates contraction of the collagen and maintains high permeability to nutrients and growth factors in a manner similar to that of short collagen fiber reinforcement pioneered by Gentleman et al. (Gentleman et al Plast Reconstr Surg 2007; 119(2):508-16; Gentleman et al. Tissue Engineering 2004; 10:421-427).

Scaffolds are prepared according to the methods outlined in Example 1 and divided into five different configurations. Collagen gels prepared with rat tail tendon-derived collagen are prepared according to standard methods and rat-derived endothelial cells are mixed within the gel at concentrations of 100,000 cells/ml or 500,000 cells/ml. After 21 days in culture, the scaffolds are fixed in 10% neutral buffered formalin, paraffin embedded and prepared for histological analysis. Hematoxylin/Eosin staining is performed in order to evaluate the formation of sinusoids within the porous collagen structure. A two-factor ANOVA is used to determine the effect of porous scaffold configuration and cell number.

Example 5

Effects of VEGF-Doped PLGA Particles on Sinusoid Formation In Vitro

The experiments described in Example 4 are repeated with the addition of VEGF-doped PLGA particles approximately 100 mm in diameter (Golub et al., Am Physiol Heart Circ Physiol 2010; 298:H1959-H1965). The small size of the PLGA particles prevents the buildup of acidic by-products and VEGF encourages blood vessel formation. The density of PLGA particles is varied (1-10 mg/ml of collagen solution) and, after 21 days in culture, the scaffolds are fixed in 10% neutral buffered formalin, paraffin embedded and prepared for histological analysis. Hematoxylin/Eosin staining is performed in order to evaluate the formation of sinusoids within the porous collagen structure. If there is a significant effect of porous scaffold configuration or cell number, the statistical analysis is augmented to include the effects of VEGF-doped PLGA particles. If there are no statistically significant effects in Example 4, a one factor ANOVA is used.

Example 6

Implantation of Porous Collagen Scaffolds into Surgically Defined Defects Within the Liver Partial hepatectomy in rats is utilized to evaluate the implantation of porous collagen scaffold (Palmes and Spiegel Biomaterials 2004; 25(9):1601-11). The first step is to anaesthetize the rat and perform a median laparatomy. The liver is then mobilized by dividing the ligaments that restrain the left and right lobes. In rats, the left and right lobes are resected and ligatures applied to the vasculature. Tightening the ligatures induces ischemia and the lobes are then resected. After resection, the implant scaffolds are implanted and sutured to the remaining lobe. In order to control bleeding, the implant is wrapped in a small intestinal submocosa (SIS) sheath and the ligature loosened to allow blood flow through the structure. This model is advantageous because the implant can be applied to the left or right lobe (chosen randomly) and the contralateral lobe can be used as an animal-specific control. In addition, wrapping the implant in a protective sheath eliminates the need to suture directly to the main blood vessels. The animals are allowed to recover and ambulate normally for about 6 to 8 weeks. Animals are then sacrificed and the tissues prepared for histological examination.

Example 7

Histological Evaluation of Three Dimensional Tissue-Engineered Implants After 6-8 Weeks In Vivo After experimental implantation of porous collagen scaffolds as described in Example 6, the animals are sacrificed, the livers removed, and fixed in 10% neutral buffered formalin for 48 hours. Thin sections (<7 mm in thickness) are obtained through the implant and liver. Hematoxylin and Eosin staining is performed in order to visualize the structure of the sinusoids and rule out the presence of degenerative processes. Subsequent sections are stained with Prussian Blue to quantify iron content, and Masson's trichrome stain is used to quantify the presence of scar tissue. Finally, glycogen and copper are evaluated using a periodic acid-Schiff stain and Rhodanine, respectively. Relative concentrations are determined based on comparisons to normal liver and fibrous tissue controls.

Example 8

Evaluation of the Ability to Control BMSC Differentiation in a Three Dimensional Scaffold that Simulates the In Vivo Environment of the Regenerating Liver In this Example, the work of Yamamoto et al. (Yamamoto et al. FEBS Journal 2008; 275:1260-1273) is extended to three dimensional cultures. Yamamoto et al. demonstrated that a combination of Hepatocyte growth factor (HGF), DMSO, and oncostatin M led to hepatocytic differentiation of BMSCs based on phenotypic markers. Later work showed that the addition of devitalized liver tissue aids in maintaining differentiation (Sellaro et al. FEBS Journal 2008; 275:1260-127).

In this Example, each factor and the incorporation of liver-derived extracellular matrix (ECM) into the biocompatible scaffold are evaluated in turn. In particular, the differentiation process is evaluated in a three dimensional culture comprising a cylindrical demineralized cancellous bone segment impregnated with BMSCs, and a collagen hydrogel with or without the devitalized ECM. It has already been established that the cancellous bone structure eliminates contraction of the collagen and maintains high permeability to nutrients and growth factors (e.g., Gentleman et al., 2004 Tiss. Eng. 10:421). Functional assessment at 7, 14, and 21 days post-differentiation is determined by measuring albumin production and by performing an ammonia challenge (Sellaro et al. FEBS Journal 2008; 275:1260-1273).

Example 9

Quantification of the Mechanical Strength of Fully Demineralized Scaffolds Subjected to Various Crosslinking Treatments Successful integration of a scaffold involves its ability to accept sutures at the locations where the base units are attached together, at the attachment points for the blood vessels, and at the interface between the engineered tissue and the host tissue. In this Example, the effects of crosslinking treatment on the mechanical properties of the scaffold are evaluated, including tension, compression, and suture pull-out strength. The suture pull-out strength is evaluated using a custom built mechanical testing system.

After demineralization, the samples are washed thoroughly in nanopure water and dried in air. The dry mass of each sample is recorded. Chemical crosslinking of the structure is then performed using one of four chemical treatments (1-ethyl-3-(3-dimethyl aminopropyl) carbodiimide (EDC), genipin, ethylene glycol diglycidyl ether, glycosaminoglycan complexing) and no-treatment controls (n=10 per treatment group as determined by a priori power analysis). Each crosslinking treatment is applied for 24, 48, 96, or 164 h. In addition to measuring the mechanical properties, it is ensured that the crosslinking treatment does not adversely affect the differentiation strategy as described in Example 8.

Example 10

Preparation of Demineralized Cancellous Bone Scaffolds

Porcine vertebral, femoral, and pelvic bone specimens were harvested from market weight animals at the Indiana Animal Disease Diagnostic Laboratory (A.D.D.L.) located at Purdue University. Specifically, samples were made of vertebral bodies, femoral head, and iliac crests all cut in the anatomical loading direction. For compression and permeability testing, the bone was machined into cylindrical samples (d=6.5 mm, h=9 mm) using Computer Numerically Controlled Junior (CNC Jr.) Table Top Mill. Degradation testing used compressive testing samples that were cut into semi-circular disks (r=3.25 mm, h=4.5 mm). For cell attachment testing, the bone was cut into rectangular prisms (3 mm×3 mm×1.5 mm) using the ISOMET® 1000 precision Sectioning Saw to make even thicknesses and then a hand saw to cut proper lengths and widths.

The demineralization process used was as described previously (Dickerson, D.A., *Development of a Naturally Derived Biomaterial with Controlled Regional Extracellular Matrix Heterogeniety for Orthopaedic Interface Regeneration* PhD Dissertation. 2009: Purdue University). Briefly, samples were soaked for 24 hours in detergent solution of 1% TERGAZYME® detergent (Alconox, White Plains, N.Y.) to remove marrow from trabecular spaces. For 24 hours the samples were soaked in acetone (100%) to de-fat and then for 12 hours in 3% hydrogen peroxide to remove osteoinductive growth factors. Samples were demineralized by soaking for 4.5 hours in a solution of 1 M hydrochloric acid and 1.9 mM ethylene diamine tetraacetic acid (50 mL per gram). For cell culture experiments, the samples were thoroughly rinsed in deionized water and then sterilized by soaking in 70% ethanol for at least 24 hours.

Example 11

Measurement and Imaging of Scaffolds

Scaffolds prepared as described in Example 10 were dried at room temperature for 24 hours, measured with a digital caliper, and weighed using an analytical balance. The volume fractions of pores and bone, referred to as porosity (Equation 1) and volume fraction (Equation 2), are calculated using the apparent density ($\rho_A$) of the entire material and the true density ($\rho_T=2\times10^6$ g/m$^3$) of bone trabeculae.

$$\phi_P = 1 - \frac{\rho_A}{\rho_T} \quad \text{Eq. 1}$$

$$\phi_B = \frac{\rho_A}{\rho_T} \quad \text{Eq. 2}$$

Image analysis of scaffolds accomplished measurement of pore size by using an IX71® inverted microscope (OLYMPUS® Corporation, Center Valley, Pa.) and QCAPTURE PRO™ version 5.0.1.26 software (QIMAGING™, Surrey, BC, Canada). Images were taken using a QCOLOR 5™ camera (OLYMPUS® Corporation, Center Valley, Pa.). Visualization of cell populations with Hoersht stain was accomplished using a confocal laser scanning microscope (NIKON®, Melville, N.Y.), using a dry 10x objective, 2.2 mm working distance. Laser parameters for DAPI were: Ex 360/40 nm, Em 460/50 nm. Imaging parameters were: 3 frame average per Z step, 1 micron per Z step, scanning −250 microns.

Example 12

Surface Area to Volume (SA/V) Calculation

A cellular solids model has been developed and validated by O'Brien et al. to accurately predict surface area to volume ratios of collagen-based scaffolds (Equation 3). This model was informed by pore size and volume fraction measurements.

$$\frac{SA}{V} = \frac{10.17\sqrt{\phi_B}}{d_{pore}} \quad \text{Eq. 3}$$

Example 13

MicroCT Imaging and Analysis

Images of compression samples for each type of bone were taken prior to demineralization using the MicroCT imaging system (Scanco Medical MicroCT 40, Bassersdorf, Switzerland) with an isotropic resolution of 16 µm, energy at 40 kVp, and integration time at 200 ms. The system was also used to do 2-D and 3-D image analysis. The microCT software uses a combination of plates and rods to model the trabecular bone structure. The measured volume fraction of each sample was used to calibrate the threshold for what grayscale value qualifies as bone. The analysis calculates trabecula thickness (Tb.Th) and spacing (Tb.Sp) by filling bone and non-bone spaces with spheres of known volume. Connectivity density (Conn.D) is found using slices of the 3-D analysis and mapping for continuity in bone regions from slice to slice.

The shape and density of porcine cancellous bone differ with site. Macroscale differences in morphology are even noticeable to the naked eye. These differences were explored with imaging, mechanical testing, permeability experiments, and degradation experiments. Qualitatively, MicroCT images revealed differences in trabeculae morphology (FIG. 1). The femoral architecture has intertwined trabeculae with nodule endings, whereas the vertebral and pelvic cancellous bone sites have rod-like connecting struts. However, the diameters of these struts appear smaller in pelvic bone compared to vertebral bone.

Quantitatively, MicroCT analysis provided data for bone volume fraction, porosity, trabecula thickness (Tb.Th), trabecula separation (Tb.Sp), and connectivity density (Conn.D)

(Table 2). These data support the described qualitative differences in trabeculae morphology and thickness. For all quantitative results, Analysis of Variance (ANOVA) at a significance level of 5% using Bonferroni-Dunn post-hoc tests for multiple comparisons was used to confirm differences among groups. Statistical significance for a given comparison is noted by a line connecting the pair marked with an asterisk which indicates a p-value of less than 0.0167 for multiple comparisons among three groups and a p-value of less than 0.05 when a single comparison between two groups.

TABLE 2

Quantitative results from MicroCT analysis of porcine cancellous bone

| | Bone Volume Fraction [1] | Porosity [1] | Tb. Th [mm] | Tb. Sp [mm] | Conn.D [1/mm$^3$] |
|---|---|---|---|---|---|
| Vertebral (n = 3) | 0.208 ± 2.68 | 0.792 | 0.076 ± 0.008 | 0.297 ± 0.051 | 19.508 ± 2.50 |
| Pelvic (n = 3) | 0.129 ± 0.69 | 0.871 | 0.056 ± 0.003 | 0.386 ± 0.010 | 17.395 ± 1.92 |
| Femoral (n = 3) | 0.338 ± 3.36 | 0.662 | 0.107 ± 0.016 | 0.214 ± 0.063 | 10.574 ± 1.31 |

The connectivity density, which is greater when trabeculae are linked together, was found to be significantly higher for vertebral (p=0.0053) and pelvic (p=0.0156) compared to femoral. This reflects the architecture of vertebral and pelvic trabeculae, which can be described as connecting rods. In contrast, the femoral trabeculae can be described as intertwined with small branches that end in nodules. Femoral had significantly larger trabecula thickness, as expected because of the nodule endings, compared to vertebral (p=0.0015) and pelvic (p=0.013).

Bone volume fractions were significantly different among all three cancellous bone sites (Table 2). The bone volume fraction of femoral was significantly higher than both vertebral (p=0.0016) and pelvic (p=0.0002), and vertebral was significantly higher than pelvic (p=0.0085). Porosity is the volume fraction of pore space and therefore has exactly the opposite trend as bone volume fraction among the sites (Equation 1 and 2). The trabecula separation of pelvic was significantly higher than femoral (p=0.0071). Trabecular spacing (Tb.Sp) was greatest in pelvic, lower for vertebral, and least in femoral. This trend mirrors volume fraction analysis as it should since more separated trabecula create a lower bone density material. Comparison of apparent density empirical measurements also show that femoral samples (n=7, 6.15×10$^5$ g/mm$^3$) were most dense followed by vertebral (n=25, 4.26×10$^5$ g/mm$^3$) and then pelvic (n=6, 2.51×10$^5$ g/mm$^3$) samples (p<0.0001).

Example 13

Crosslinking Treatment

Chemical crosslinking was performed using 1-ethyl-3-(3-dimethyl aminopropyl) carbodiimide (EDC, Fluka Chemie AG, Buchs, Switzerland) and a modified protocol previously described (Dickerson, D. A., *Development of a Naturally Derived Biomaterial with Controlled Regional Extracellular Matrix Heterogeneity for Orthopaedic Interface Regeneration* PhD Dissertation. 2009: Purdue University; Pieper, J. S., et al., Biomaterials, 1999. 20(9):847-858). The demineralized bone scaffolds were soaked for 30 minutes in 50 mM 2-morpholinoethane sulphonic acid (MES, Fluka Chemie, AG, Buchs, Switzerland) and then placed in a 33 mM solution of EDC containing 50 mM MES and 6 mM N-hydroxysuccinimide (Fluka Chemie, AG, Buchs, Switzerland) for 4 hours. After, the samples were washed twice in 0.1 M Na$_2$HPO$_4$ for 1 hour, and then 1 M NaCl for 2 hours, and finally 2 M NaCl for 1 day followed by rinsing with deionized water.

Example 14

Heparin Treatment

Heparin was incorporated into the demineralized bone scaffold as previously described (Yao, C. et al. Biomaterials, 2006. 27(8):1608-1616). Briefly, 1 mg of heparin (H-4784; SIGMA®) was activated with 1 mg EDC/0.6 mg NHS in 500 .mu.L of 0.05 M MES buffer pH 5.6 for 10 minutes. While immersed in this solution, bubbles were removed using a vacuum bell pressurized to 20 mmHg for 2 minutes. The reaction continued for 4 hours and then the scaffolds were washed in 0.1M Na$_2$HPO$_4$ (2 hours), 4 M NaCl (4 times in 24 hours), and distilled water (5 times in 24 hours).

Example 15

Heparin and Chitosan Treatment

Chitosan was added to the heparinized scaffolds by slight modification of a layer by layer process previously described (Meng, S. et al. Biomaterials, 2009. 30(12):2276-2283). Briefly, heparinized scaffolds were immersed in a solution of 0.2 wt % acetic acid and 0.1 wt % chitosan (Super-Grow Scientific Plant Products, LaSalle, Canada) with a deacetylation degree of 85% followed by rinsing with deionized water. The next layer of heparin was added by immersing the scaffolds in a solution of 0.1 wt % heparin sodium salt for 15 minutes followed by rinsing with deionized water. The chitosan/heparin layering process was repeated until 10 layers of heparin and chitosan were deposited by electrostatic interaction to produce a supramolecular complex.

Heparin Verification

The amount of heparin immobilized was determined by a previously described assay (Steffens G. C. M. et al. Tissue Engineering, 2004. 10(9-10):1502-1509). Scaffolds were thoroughly rinsed in deionized water and then immersed for 4 hours in 3 mL of a solution containing 0.1M HCl, 2 mg/mL NaCl, and 0.4 mg/mL toluidine blue zinc chloride double salt resulting in a toluidine blue-heparin bound complex. Samples were rinsed in deionized for 24 hours, and then the toluidine blue complexed to heparin was solubilized with 3 mL of a 1:4 (v/v) mixture of 0.1M NaOH and ethanol. Absorbance of the solution was determined using a spectrophotometer at 530 nm (THERMOSCIENTIFIC®, Waltham, Mass.) after 1:5 dilution with the NaOH/ethanol solution.

The verification of heparin and heparin/chitosan coatings (n=6) was performed by measuring the amount of toluidine blue bonded to heparin. The absorbance of heparinized scaffolds (0.276) was significantly higher than heparin/chitosan (0.238, p=0.0016) and uncoated (0.087, p<0.0001) groups, and heparin/chitosan had significantly higher absorbance than uncoated (p<0.0001). It is hypothesized that since heparin is sandwiched between chitosan layers, the heparin was less accessible in the heparin/chitosan bilayer coatings.

Example 15

Mechanical Testing

Using a mechanical testing system (Test Resources 100Q) in the Weldon School of Biomedical Engineering undergraduate laboratory, the compression testing samples were preloaded 0.05 N and then compressed to 50% of initial sample length at a displacement rate of 2.5 mm/min.

Figure 2:
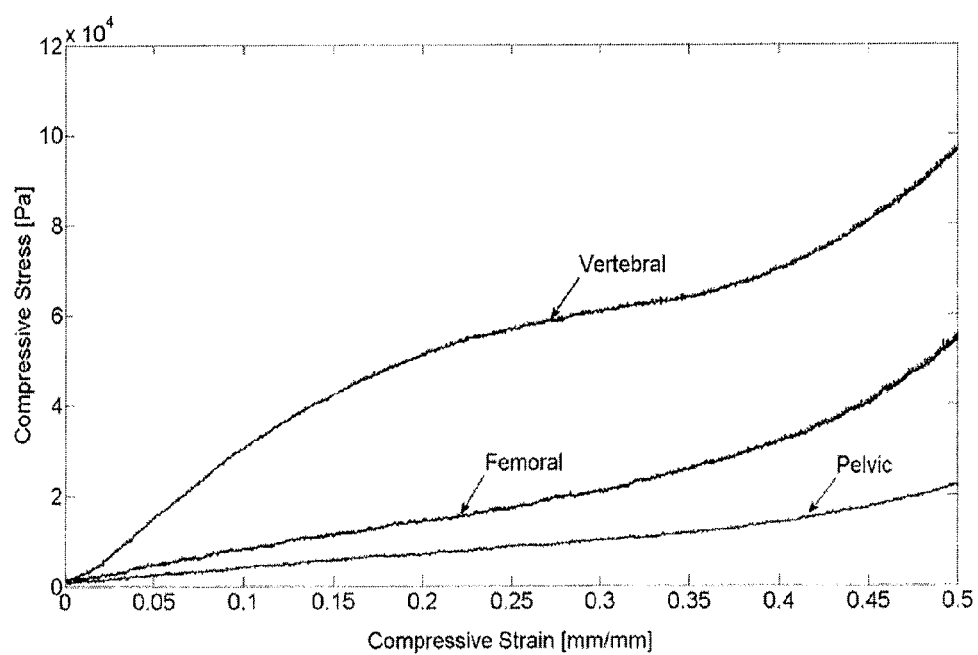
FIG. 2 shows compressive stress-strain curves for demineralized cancellous bone.
Figure 3:
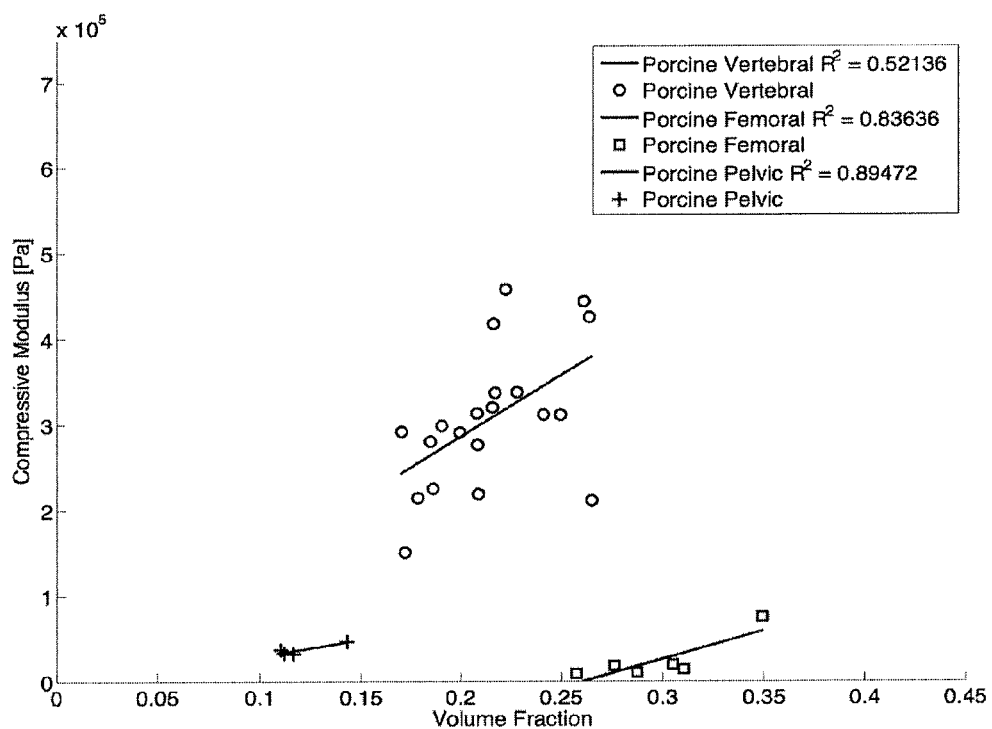
FIG. 3 is a plot of compressive tissue modulus as a function of volume fraction for various demineralized cancellous bone.

Samples were demineralized and tested in compression resulting in stress-strain curves with differing features (FIG. 2). Pelvic and femoral stress-strain curves had nearly linear relationships until stiffening at 35% deformation whereas vertebral showed softening around 10% deformation before stiffening at 35% deformation. The compressive tissue modulus was significantly higher for vertebral samples ($2.94 \times 10^5$ Pa) compared to pelvic ($5.74 \times 10^4$ Pa) and femoral ($2.44 \times 10^4$ Pa) samples (p<0.0001). For scaffolds from all bone sites, the volume fraction had an effect on tissue modulus such that the greater the volume fraction the greater the tissue modulus (FIG. 3).

Example 16

Permeability Testing

Cylindrical bone samples were placed into the bottom of a 10 mL pipette tube. Samples were positioned securely so as to form a tight seal with the tube, the bottom was covered to prevent leakage, and 10 mL of PBS was added to the tube. A timer was started at the moment that the tube was uncovered, and times taken to reach the volumes of 7, 4, and 0 mL of PBS were recorded. Permeability testing was performed three times for each sample.

These data were used to find the pressure due to the remaining volume of fluid as a function of time. The atmospheric pressures cancel since both the top and bottom of the tube are open during the experiment. The fluid is driven through the material by the hydrostatic pressure. Equation 4 shows the Darcy velocity, and Equation 5 shows the volumetric flow rate in terms of hydrostatic pressure and a group of constants: permeability k, cross-sectional area A, sample length L, and viscosity $\mu$. Permeability is found after integrating the volumetric flow rate and solving this closed integral (Equations 6 and 7).

$$u_D = \frac{Q}{A} = \frac{k\Delta p}{\mu L_S} \quad \text{Eq. 4}$$

$$Q = u_D A = \frac{kA\Delta p}{\mu L_S} = \frac{kA\rho g h}{\mu L_S} \quad \text{Eq. 5}$$

$$V = \int_{t_o}^{t_f} Q(t) dt = \frac{kA}{\mu L_S} \int_{t_o}^{t_f} \rho g h(t) dt \quad \text{Eq. 6}$$

$$k = \frac{V \mu L_S}{\rho g A} \left( \frac{1}{\int_{t_o}^{t_f} h(t) dt} \right) \quad \text{Eq. 7}$$

When considering tissue engineering applications that involve larger scaffold volumes, mass transport becomes a limiting factor. One predictor of nutrient transport is permeability which is the measure of how fluid passes through the porous material. Results of this testing showed that vertebral ($6.03 \times 10^{-10}$ mm$^2$, p=0.0068) and pelvic ($7.12 \times 10^{-10}$ mm$^2$, p=0.0032) samples were significantly more permeable than femoral ($3.01 \times 10^{-10}$ mm$^2$) samples.

Figure 4:
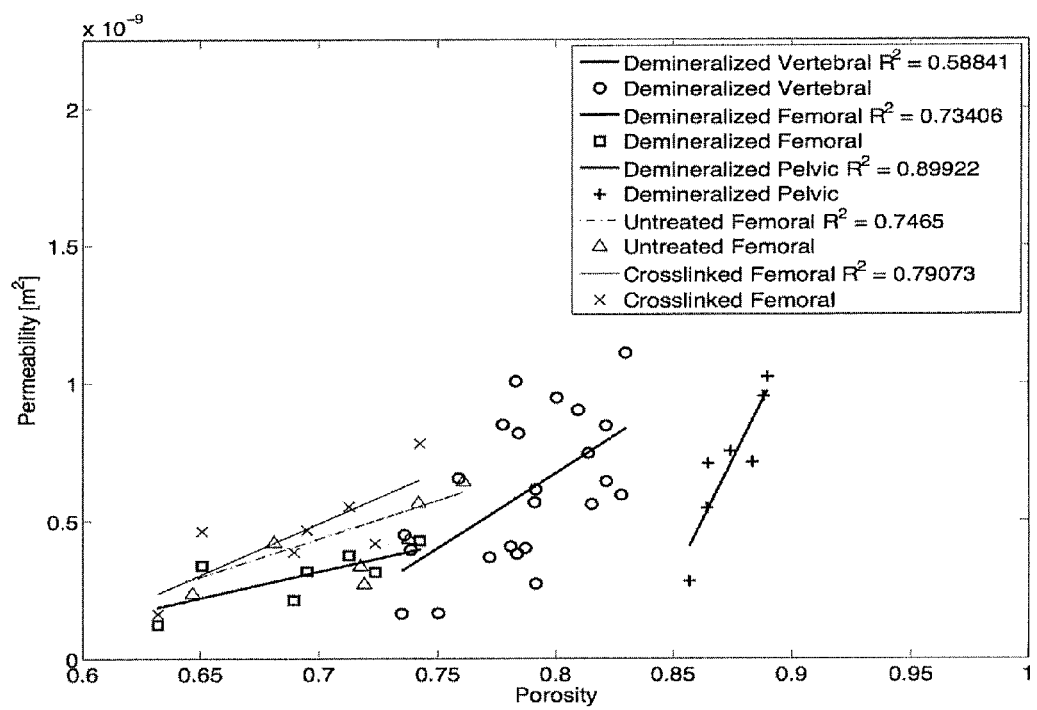
FIG. 4 is a plot of porosity as a function of permeability.

The porosity of each sample was also calculated (Equation 1) and plotted with permeability (FIG. 4). The overall trend was for more porous materials to be proportionally more permeable; however, this trend was not equally correlated for every sample type. The vertebral bone samples upheld this trend of porosity and permeability increasing proportionally, whereas pelvic bone samples had sharply increasing permeability despite minor changes in porosity. Conversely, the femoral bone samples had persistently low permeability that did not change in proportion with porosity.

Figure 5:
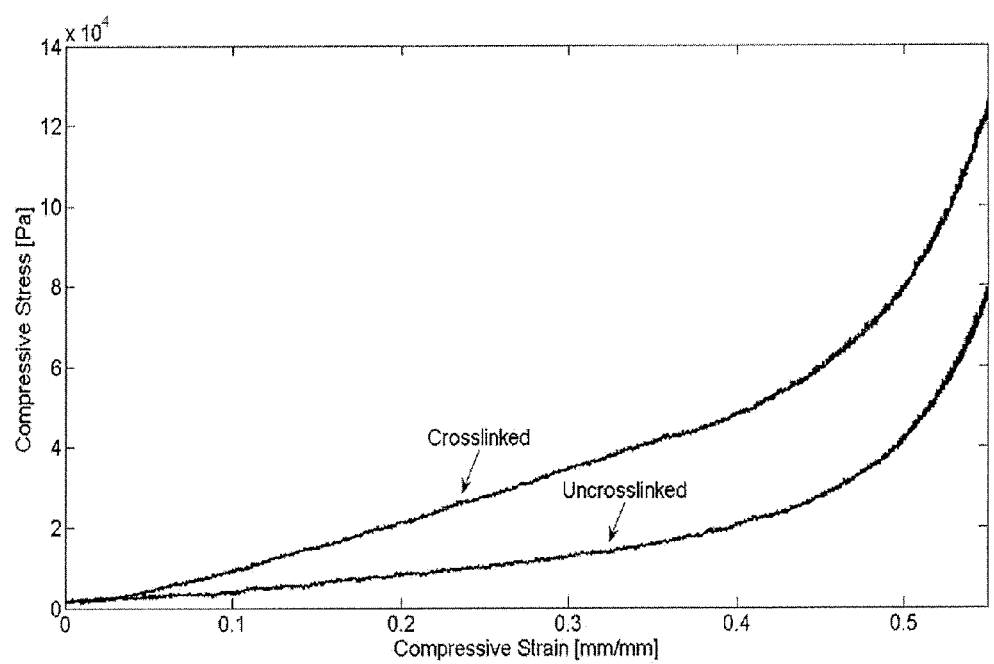
FIG. 5 shows compressive stress-strain curves for crosslinked and uncrosslinked samples.

Ideally, scaffolds should be capable of adapting to suit various tissue engineering applications. To demonstrate the naturally-derived scaffold's modifiable strength, crosslinking treatments were carried out on porcine femoral samples. The stress-strain curves of crosslinked and uncrosslinked samples had similar shapes but varying moduli (FIG. 5). The crosslinked samples ($1.18 \times 10^5$ Pa) had a significantly higher compressive tissue modulus than uncrosslinked samples ($2.44 \times 10^4$ Pa) (n=6, p=0.0159). Permeability was unchanged throughout these processes. Comparison of permeability found no significant differences among uncrosslinked ($3.01 \times 10^{-10}$ m$^2$), crosslinked ($4.62 \times 10^{-1}$ m$_2$), and untreated (mineral content intact) ($4.14 \times 10^{-10}$ m$^2$) groups (p>0.0167). Additionally, permeability versus porosity relationships for uncrosslinked, crosslinked, and untreated (mineral content intact) samples were similar. Therefore, strength was increased while maintaining permeability. In summary, femoral scaffolds had low stiffness and permeability, pelvic had similarly low stiffness but high permeability, vertebral scaffolds have both high stiffness and high permeability. Crosslinking treatment increases scaffold stiffness without altering permeability.

Example 17

Degradation

Scaffolds were incubated with crude collagenases secreted from *Clostridium histolyticum* (C0130; SIGMA®, 255 U/mg collagenase activity); this mixture contains collagenase, non-specific proteases and clostripain. For a scaffold weighing 10 mg, 0.5 mL of 0.1M Tris-HCl buffer (pH 7.4) containing 0.005 M CaCl, and 0.05 mg/MI sodium was added. After incubating at 37° C. for one hour, 0.5 mL of collagenase solution (200 U/mL) in Tris-HCl buffer was added final collagenase concentration of 100 U/mL. Scaffolds were dried and weighed after 12, 36, and 60 hours.

In addition to high strength and permeability, scaffolds must resorb at a rate that complements the wound healing process for a given application. Enzymatic degradation, an important predictor of bioabsorption, was investigated by incubating scaffolds in a collagenase solution. Crosslinking treatment extended degradation time such that uncrosslinked scaffolds degraded within 12 hours whereas crosslinked scaffolds took around 60 hours (Table 3). After 60 hours in solution, pelvic scaffolds still had 46% of initial mass while vertebral scaffolds had less than 3% of initial mass and femoral scaffolds were fully degraded (Table 3). This demonstrates that the degradation process of the naturally-derived scaffold can be tuned by material selection and crosslinking to meet the timeline of specific wound healing applications.

TABLE 3

| | Percentage of Initial Mass | | | |
|---|---|---|---|---|
| Degradation Time (hours) | Uncrosslinked (n = 6) | Crosslinked Vertebral (n = 6) | Crosslinked Femoral (n = 3) | Crosslinked Pelvic (n = 3) |
| 0 | 100% | 100% | 100% | 100% |
| 12 | 0%* | 22.9% | 48.6% | 54.7% |
| 36 | 0%* | 8.3%* | 9.2% | 46%* |
| 60 | 0% | 2.4% (*pelvic) | 0% (*pelvic) | 40.4%* |
| Coefficient from Exponential Fit | 0* | −0.041 ± 0.028 | −0.081 ± 0.003* | −0.007 ± 0.004* |

Example 18

Cell Culture

Human Aortic Endothelial Cells were cultured in Endothelial Basal Medium (EBM-2, LONZA®, Walkersville, Md.) supplemented with 10% Fetal Bovine Serum (FBS, INVITROGEN®, Carlsbad, Calif.), 1% Penicillin-Streptomycin (10 mg/mL Pen-Strep, SIGMA®, St. Louis, Mo.), and 0.1% Amphotericin-B (250 μg/mL Amp-B, SIGMA®, St. Louis, Mo.). Rat Fibroblasts (RFB) and Murine Bone Marrow Stem Cells (D1) were cultured in Dulbecco's Modified Eagle's Medium (1×DMEM, Invitrogen, Carlsbad, Calif.) supplemented with 10% FBS, 1% Pen-Strep, and 0.1% Amp-B. All cells were stored in a humidified 37° C., 5% $CO_2$ incubator.

Example 19

Cell Attachment and Proliferation

Sterile demineralized bone samples were placed into 24 well plates (BD® Biosciences, San Jose, Calif.) and then $10^5$ cells suspended in media (190 μL) were pipetted onto the scaffold. After 4 hours, 7, or 30 days, the samples were rinsed in phosphate buffered saline (PBS) for one minute. Then, the samples were submerged into 150 μL of 1% TRITON™-X solution (SIGMA®, St. Louis, Mo.) in order to lyse the cells and release lactate dehydrogenase (LDH). LDH activity compares relative cell number and was measured using CytoTox 96® Non-Radioactive Cytotoxicity Assay (Promega Corporation, Madison, Wis.). The absorbance readings were found by using a spectrophotometer (THERMOSCIENTIFIC®, Waltham, Mass.) at 492 nm.

Figure 6:
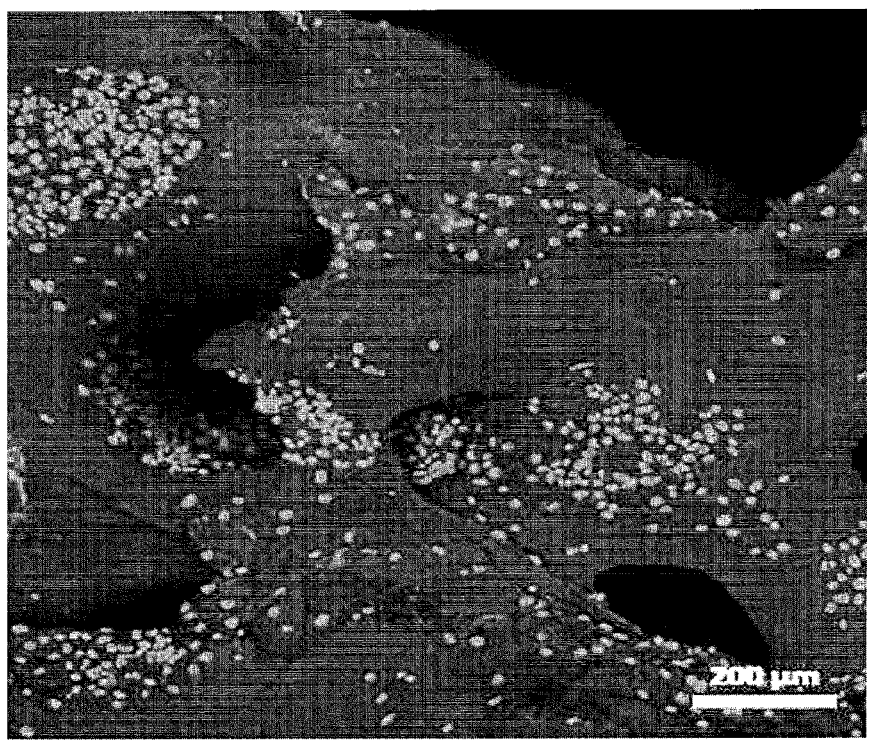
FIG. 6 is an image of a scaffold with Hoechst stained, rat fibroblast cells attached.

Various scaffold-cell interactions were investigated to inform material selection for the wide range of tissue engineering applications. One such interaction, cell attachment of rat fibroblasts to a porous scaffold derived from porcine vertebral bone is shown in FIG. 6. This image was obtained using a confocal laser scanning microscope that scanned down 250 microns and captured cell populations both on the surface and interior of the scaffold by peeking through the pores. Pore sizes at the surface of scaffolds were measured using an inverted microscope and imaging software (Table 3.3). These measurements informed a cellular solids model that has been developed by O'Brien et al. to predict surface area available for cell attachment in collagen-based materials (Equation 3). The model calculated the SAN ratio for scaffolds derived from femoral bone to be the highest, followed by pelvic and then by vertebral scaffolds (Table 4).

TABLE 4

| | Bone Volume Fraction [1] | Porosity [1] | Pore Size [μm] | $\frac{SA}{V} = \frac{10.17\sqrt{\phi_B}}{d_{pore}}$ |
|---|---|---|---|---|
| Vertebral (n = 3) | 0.205 ± 2.68 | 0.795 | 951 ± 286 | .0048 |
| Pelvic (n = 3) | 0.132 ± 0.69 | 0.868 | 613 ± 217 | .0060 |
| Femoral (n = 3) | 0.262 ± 3.36 | 0.738 | 695 ± 176 | .0075 |

Increased surface area provides more space for cell attachment; however, the SAN relationship among bone sources was not identically matched by cell attachment results. This highlights the impact of microarchitecture and surface shape on cell attachment. The LDH activity measured after Fibroblast cell attachment to pelvic (0.354) scaffolds was significantly higher than attachment to vertebral (0.249) and femoral (0.229) scaffolds (n=6, p<0.0001). Vertebral and femoral scaffolds were not significantly different (p>0.0167).

Cell attachment studies of the coated scaffolds were performed with rat fibroblasts (RFB), murine bone marrow stem cells (BMSC), and human aortic endothelial cells (HAEC) (n=6). For RFB, heparinized scaffolds promoted significantly more cell attachment than crosslinked scaffolds (p=0.0072). BMSC attached significantly more to heparinized and heparin/chitosan coated scaffolds than uncrosslinked (p<0.0001) and crosslinked (p=0.0004 and p<0.0001) scaffolds. HAEC responded significantly different to each coating with the order of response from highest to lowest being heparin/chitosan, heparin, crosslinked, and uncrosslinked scaffolds (p<0.0001). The proliferation of BMSC in crosslinked scaffolds derived from vertebral bone was significantly higher compared to uncrosslinked after 30 days (n=6, p<0.0001). Additionally, the scaffolds maintained strength and initial volume throughout this period of cell growth.

Example 20

Scaffold Design Considerations

Stiffness, permeability, and degradation differ among the sources. Additionally, the stiffness and degradation times can be increased by crosslinking treatments without altering scaffold permeability. The differing properties of porcine cancellous bone sources allows flexibility in scaffold design. For example, for a soft tissue application for which slow degradation and high elasticity are indicated, crosslinked vertebral scaffolds would have the requisite slow degradation rate but may be too rigid. In contrast, pelvic bone sources would be able to provide slow degradation without becoming rigid from crosslinking treatment.

The cell interactions were also shown to differ among bone sources sites. The importance of both pore size and shape was demonstrated by comparing a theoretical model with experimental cell attachment data for scaffolds of varying shapes and pore sizes. The model calculation of the SA/V ratio was informed by pore size and volume fraction measurements which provide a valid estimate of scaffold shape and binding characteristics for most collagen-based materials. However, the results demonstrate the anomalous nature of femoral bone which has thick nodules evidenced by high SA/V ratio but is a mechanically weak, disconnected material (FIG. 2). It is hypothesized that cells attached to pelvic and vertebral bone to a greater extent despite their lower SAN ratios because these structures have higher interconnectivity (Table 2).

The proper tuning of surface chemistry can selectively attach certain cell types and promote specific responses. Fibroblasts are known mediators of wound healing. For tissue regeneration, stem cells can be differentiated and encouraged to proliferate. Endothelial cells are important for applications requiring vascularized tissue or for the application of blood vessel replacement specifically. Heparinization via crosslinking of the naturally-derived scaffold was performed to gather anticoagulant properties and to add a surface coating that can bind to many other molecules, growth factors, proteins, peptides, etc. Chitosan demonstrates this binding and was used to create a heparin/chitosan bilayer of 10 layers of each. Cell attachment studies with these coatings revealed the differing preferences of RFB, BMSC, and HAEC.

Example 21

Statistical Analysis

STATVIEW® software (Version 5.0.1, SAS Institute Inc.) was used to compute all statistical analyses. Analysis of Variance (ANOVA) was performed at a significance level of 5% using Bonferroni-Dunn post-hoc tests for multiple comparisons.

The various embodiments described above can be combined to provide further embodiments. All of the U.S. patents, U.S. patent application publications, U.S. patent applications, foreign patents, foreign patent applications and nonpatent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A biocompatible scaffold substantially free of mineralized bone comprising demineralized cancellous bone substantially devoid of all osteoinductive factors, the demineralized cancellous bone comprising at least a first region and a second region, wherein a concentration gradient of crosslinks is configured to extend between the first region to the second region such that the concentration of the crosslinks in the first region is substantially higher than the concentration of the crosslinks in the second.

2. The biocompatible scaffold of claim 1, wherein the first region has increased mechanical strength relative to the second region.

3. The biocompatible scaffold of claim 1, wherein the first region comprising stiffened demineralized bone has greater resistance to enzymatic degradation relative to the second region.

4. The biocompatible scaffold of claim 1, wherein the biocompatible scaffold contains cells.

5. The biocompatible scaffold of claim 4, wherein the cells include stem cells and/or cells from soft tissue.

6. The biocompatible scaffold of claim 5, wherein the soft tissue is selected from liver, pancreas, skin, bladder, kidney, tendon, ligament, fascia, fibrous tissues, adipose tissue, intestinal tissue, synovial membranes, muscles, nerves, blood vessels, cartilage, meniscal tissue, periosteal tissue, pericardial tissue, synovial tissue, bone marrow, spleen tissue, intervertebral disc tissue, embryonic tissue, periodontal tissue, vascular tissue, blood and combinations thereof.

7. The biocompatible scaffold of claim 5, wherein the stem cells are umbilical cord blood-derived stem cells or adult stem cells selected from hematopoietic stem cells, bone marrow stem cells, adipose-derived stem cells, mesenchymal stem cells, and soft tissue-derived stem cells, or a combination thereof.

8. The biocompatible scaffold of claim 1, further comprising a hydrogel within the scaffold.

9. The biocompatible scaffold of claim 1, further comprising a polymer within the scaffold.

10. The biocompatible scaffold of claim 1, further comprising a biomolecule or agent capable of promoting cell growth or differentiation, tissue repair, promoting healing and/or regeneration of tissue, preventing infection, reducing inflammation, preventing or reducing adhesion formation, or suppressing immune response.

11. The biocompatible scaffold of claim 1, wherein the scaffold comprises surface chemistry comprising at least one of covalently attached biomolecules and adsorbed biomolecules.

12. The biocompatible scaffold of claim 1, wherein the scaffold comprises a surface that has texture, roughness, or three-dimensional unevenness produced by one or more of chemical etching, physical etching, and laser etching.

13. The biocompatible scaffold of claim 1, wherein at least a portion of some or all regions is encapsulated by a biocompatible layer.

14. The biocompatible scaffold of claim 13, wherein the biocompatible layer is semipermeable.

15. The biocompatible scaffold of claim 13, wherein the biocompatible layer is bioresorbable.

16. The biocompatible scaffold of claim 13, wherein the biocompatible layer is a collagen matrix.

17. The biocompatible scaffold of claim 13, wherein the biocompatible layer is small intestine submucosa.

18. A method for repairing or regenerating tissue comprising implanting in the tissue in need of repair or regeneration, a biocompatible scaffold of claim 1.

19. The method of claim 18, wherein the tissue comprises organ tissue, abdominal wall, pericardium, a hernia, bone, perichondrium, intervertebral disc, articular cartilage, dermis, epidermis, bowel, ligaments, tendons, vascular tissue, heart valve, venous valve, esophagus, trachea, intestine, fallopian tube, liver, pancreas, skin, bladder, kidney, fascia, fibrous tissues, adipose tissue, muscle, nerves, blood vessels, cartilage, meniscal tissue, periosteal tissue, pericardial tissue, synovial tissue, bone marrow, spleen tissue, embryonic tissue, or periodontal tissue.

* * * * *